United States Patent
Pedroso et al.

(10) Patent No.: US 10,314,944 B2
(45) Date of Patent: Jun. 11, 2019

(54) XENOGRAFT SOFT TISSUE IMPLANTS AND METHODS OF MAKING AND USING

(71) Applicants: Pedro Daniel Pedroso, Gainesville, FL (US); Amanda Michele Ely, Newberry, FL (US)

(72) Inventors: Pedro Daniel Pedroso, Gainesville, FL (US); Amanda Michele Ely, Newberry, FL (US)

(73) Assignee: RTI Surgical, Inc., Alachua, FL (US)

( * ) Notice: Subject to any disclaimer, the term of this patent is extended or adjusted under 35 U.S.C. 154(b) by 0 days.

(21) Appl. No.: 13/828,363

(22) Filed: Mar. 14, 2013

(65) Prior Publication Data

US 2013/0302435 A1    Nov. 14, 2013

Related U.S. Application Data

(60) Provisional application No. 61/646,229, filed on May 11, 2012.

(51) Int. Cl.
    *A61L 27/36* (2006.01)

(52) U.S. Cl.
    CPC ....... *A61L 27/3687* (2013.01); *A61L 27/3662* (2013.01); *A61L 2430/10* (2013.01); *A61L 2430/40* (2013.01)

(58) Field of Classification Search
    CPC ............. A61L 27/3687; A61L 27/3662; A61L 2430/10; A61L 2430/40
    USPC ....................................................... 435/325
    See application file for complete search history.

(56) References Cited

U.S. PATENT DOCUMENTS

| | | |
|---|---|---|
| 5,263,984 A | 11/1993 | Li et al. |
| 5,556,428 A | 9/1996 | Shah |
| 5,595,571 A | 1/1997 | Jaffe |
| 5,607,476 A | 3/1997 | Prewett |
| 5,718,012 A * | 2/1998 | Cavallaro ................ 8/94.11 |
| 5,769,893 A | 6/1998 | Shah |
| 5,782,914 A | 7/1998 | Schankereli |
| 5,865,849 A | 2/1999 | Stone |
| 5,902,338 A | 5/1999 | Stone |
| 5,913,900 A | 6/1999 | Stone |
| 5,922,027 A | 7/1999 | Stone |
| 5,944,755 A | 8/1999 | Stone |
| 5,984,858 A | 11/1999 | Stone |
| 5,993,844 A | 11/1999 | Abraham |
| 6,024,735 A | 2/2000 | Wolfinbarger, Jr. |
| 6,049,025 A | 4/2000 | Stone |
| 6,093,204 A | 7/2000 | Stone |
| 6,110,206 A | 8/2000 | Stone |
| 6,214,054 B1 | 4/2001 | Cunanan |
| 6,231,608 B1 | 5/2001 | Stone |
| 6,267,786 B1 | 7/2001 | Stone |
| 6,270,723 B1 | 8/2001 | Laugharn, Jr. |
| 6,293,970 B1 | 9/2001 | Wolfinbarger, Jr. |
| 6,383,732 B1 | 5/2002 | Stone |
| 6,402,783 B1 | 6/2002 | Stone |
| 6,455,309 B2 | 9/2002 | Stone |
| 6,534,004 B2 | 3/2003 | Chen |
| 6,569,200 B2 | 5/2003 | Wolfinbarger, Jr. |
| 6,635,222 B2 | 10/2003 | Kent |
| 6,682,760 B2 | 1/2004 | Noff |
| 6,758,865 B1 | 7/2004 | Stone |
| 6,972,041 B1 | 12/2005 | Stone |
| 7,064,187 B2 | 6/2006 | Stone |
| 7,550,152 B2 | 6/2009 | Pandit |
| 7,594,934 B2 | 9/2009 | Stone |
| 7,595,377 B2 | 9/2009 | Stone |
| 7,648,676 B2 * | 1/2010 | Mills ................ A61F 2/08 134/26 |
| 7,674,289 B2 | 3/2010 | Xu |
| 7,722,672 B2 | 5/2010 | Stone |
| 7,824,447 B2 | 11/2010 | Xu |
| 2002/0087211 A1 | 4/2002 | Stone et al. |
| 2003/0035843 A1 | 2/2003 | Livesey et al. |
| 2003/0193104 A1 | 10/2003 | Melican et al. |

(Continued)

FOREIGN PATENT DOCUMENTS

| | | |
|---|---|---|
| CN | 101496812 A | 8/2009 |
| RU | 2440057 C1 | 1/2012 |

(Continued)

OTHER PUBLICATIONS

Stone et al., Replacement of Human Anterior Cruciate Ligaments with Pig Ligaments: A Model for Anti-Non-Gal Antibody Response in Long-Term Xenotransplantation, Transplantation, vol. 83, No. 2, Jan. 27, 2007.*

Livingston, Where do we go from here?—Santa Gertrudis Cattle in the 21st Century and beyond, The Cattle Blog, Apr. 25, 2011, Available online at: thecattleblog.blogspot.com/2011/04/where-do-we-go-from-here-santa.html.*

Seto et al., Radioprotection of Tendon Tissue via Crosslinking and Free Radical Scavenging, Clin Orthop Relat Res (2008) 466:1788-1795.*

Donahue et al., Comparison of Viscoelastic Structural, and material Properties of Double-Looped Anterior Cruciate Ligament Grafts Made from Bovine Digital Extensor and Human Hamstring Tendons, Journal of Biomechanical Engineering, vol. 123, Apr. 2001, pp. 162-169.*

(Continued)

*Primary Examiner* — Jennifer M. H. Tichy
(74) *Attorney, Agent, or Firm* — McAndrews, Held & Malloy, Ltd.

(57) ABSTRACT

The present application is directed to the field of implants comprising soft tissue for use in implantation in humans. The soft tissue implants of the present application are preferably obtained from xenograft sources. The present application provides a chemical process that neutralizes, removes or substantially reduces antigens from and sterilizes and/or strengthens xenograft implants. The present techniques yield soft tissue implants having superior structural, mechanical, and/or biochemical integrity. The present application is also directed to processes for treating xenograft implants comprising soft tissues such as tendons and ligaments, and to implants produced by such processes.

9 Claims, 6 Drawing Sheets

(56) References Cited

U.S. PATENT DOCUMENTS

| | | |
|---|---|---|
| 2005/0260107 A1 | 11/2005 | Jackson et al. |
| 2009/0269741 A1 | 10/2009 | Barendse et al. |
| 2010/0030340 A1 | 4/2010 | Wolfinbarger et al. |
| 2011/0059178 A1 | 3/2011 | Semler et al. |
| 2011/0070204 A1 | 3/2011 | Elias |

FOREIGN PATENT DOCUMENTS

| | | |
|---|---|---|
| WO | 2009079211 A1 | 6/2009 |
| WO | 2012/021814 | 2/2012 |

OTHER PUBLICATIONS

PCT, Notification of Transmittal of the International Search Report and the Written Opinion of the International Searching Authority, in International application No. PCT/US13/31427, dated May 28, 2013.

Kew et al., "Regeneration and repair of tendon and ligament tissue using collagen fibre biomaterials"; Acta Biomaterialla; published online Jun. 13, 2011; vol. 7; pp. 3237-3247, p. 3242, col. 1, para 2-3; Table 1.

PCT, Notification Concerning Transmittal of International Preliminary Report on Patentability, in International application No. PCT/US2013/031427 dated Nov. 20, 2014 (8 pages).

Conner et al. Tensioning of Anterior Cruciate Ligament Hamstring Grafts: Comparing Equal Tension Versus Equal Stress. Arthroscopy. Dec. 2008;24(12): 1323-1329.

Galili, Uri. The alpha-gal epitope and the anti-Gal antibody in xenotransplantation and in cancer immunotherapy. Immunology and Cell Biology. 2005, 83: 674-686.

Hamner et al. Hamstring Tendon Grafts for Reconstruction of the Anterior Cruciate Ligament: Biomechanical Evaluation of the Use of Multiple Strands and Tensioning Techniques. The Journal of Bone & Joint Surgery. 1999; 81:549-57.

Marumo et al. The "ligamentization" process in human anterior cruciate ligament reconstruction with autogenous patellar and hamstring tendons: a biochemical study. Am J Sports Med. Aug. 2005;33(8):1166-73. (Epub Jul. 6, 2005).

Noyes et al. Biomechanical analysis of human ligament grafts used in knee-ligament repairs and reconstructions. J Bone Joint Surg Am. 1984;66:344-352.

Noyes et al. The strength of the anterior cruciate ligament in humans and Rhesus monkeys. J Bone Joint Surg Am. 1976;58:1074-1082.

Scheffler et al. Graft remodeling and ligamentization after cruciate ligament reconstruction. Knee Surg Sports Traumatol Arthrosc. Sep. 2008;16(9):834-42. (Epub May 31, 2008).

Scranton et al. Mechanisms of anterior cruciate ligament neovascularization and ligamentization. Arthroscopy. Oct. 1998;14(7):702-16.

Wang et al. Artificial biological ligament: Its making, testing, and experimental study on animals. Microsurgery, Jan. 2008, 28(1): 44-53.

Woo et al. Tensile properties of the human femur-anterior cruciate ligament-tibia complex: The effects of specimen age and orientation. Am J Sports Med. Jun. 1991; 19(3): 217-225.

Woo et al. Healing and repair of ligament injuries in the knee. J Am Acad Orthop Surg. Nov.-Dec. 2000;8(6): 364-72.

Supplementary European Search Report corresponding to European Patent Application No. EP 13 78 7000, dated Feb. 22, 2016.

First Office action corresponding to Chinese Patent Application No. 2013800369467 dated Dec. 28, 2015.

Xie Xizhong et al., "Tendon transplantation treated with glutaraldehyde and profound hypothermia to repair hand tendon defects." Chinese Journal of Microsurgery, vol. 26, No. 4, pp. 305-306.

A Chauveau, The comparative anatomy of the domesticaled animals, New York, D Appleton and company, 1890.

V.I. Chueshov. Industrial technology of medicaments, vol. 1, Kharkov, NFAU publishers, 2002.

Nelia Patricia Garcia-Morales, Effect of Muscle Architecture in Response to Gradual Lengthening, Dec. 2007.

Aaron Seto, MS et al., Radioprotection of Tendon Tissue via Crosslinking and Free Radical Scavenging, Clin Orthop Relat Res (2008).

Chinese Office Action, dated Aug. 19, 2016.

Russia Office Action dated Dec. 23, 2016.

Official Action issued by Russian Federation for Application No. 2014150029, dated Aug. 30, 2017.

Office Action for Application No. 13 787 000.2, dated Jan. 26, 2018, 6 pages.

P.D. Hoang et al., Passive mechanical properties of human gastrocnemius, muscle fascicles and tendons in vivo, Journal of Experimental Biology, 210, 4159-4168, published by The Company of Biologists 2007.

Official Action issued by Russian Federation for Application No. 2014150029, dated Jan. 15, 2018.

\* cited by examiner

FIG. 1

Shape Cutoff: Major/Minor Ratio = MMR

MMR ≤ 3.5 (Elliptical CSA)    MMR > 3.5 (Rectangular CSA)

Weighted CSA = CSA (AMIR^Shape Weight)

$$AMIR = \frac{\text{Area Moment of Inertia about y-axis}}{\text{Area Moment of Inertia about x-axis}} = \frac{\text{Average Major}^2}{\text{Average Minor}^2}$$

Predicted UTF = 0.2415 (Weighted CSA) × LD^LD Power + 1546

| Shape | Shape Weight | LD Power |
|---|---|---|
| Elliptical | 0.50153 | 1.770 |
| Rectangular | -0.30995 | 2.237 |

Looped Implant – Pull Force Data

Bovine Implant ~1200 N greater than "High" Mean Autograft (p-value < 0.01)

Probability of being stronger than Native ACL: 98.6%

Hamner (1999), Conner (2008): 4-Strand Hamstring Autograft
Noyes (1976), Woo (1991): Native ACL

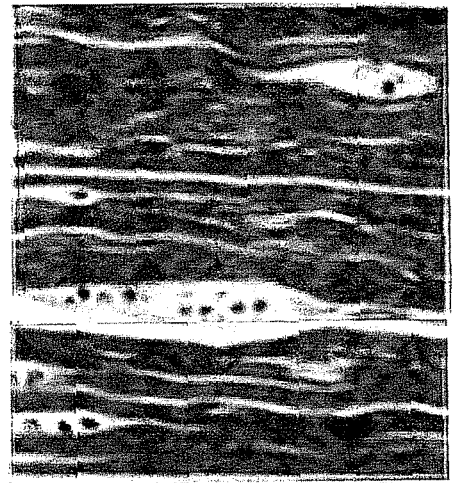
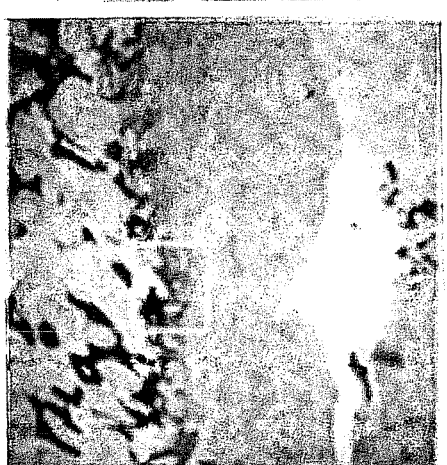
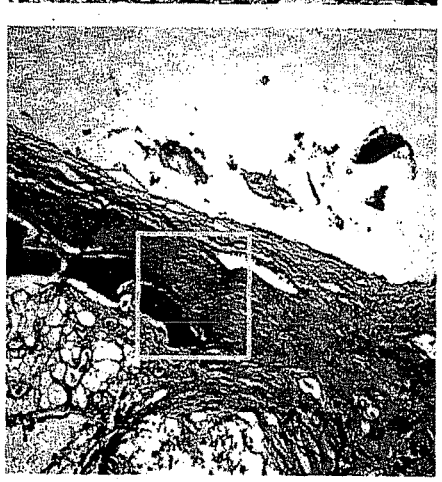

XENOGRAFT SOFT TISSUE IMPLANTS AND METHODS OF MAKING AND USING

RELATED APPLICATIONS

This application relates to and claims priority benefits from U.S. Provisional Patent Application Ser. No. 61/646,229, filed May 11, 2012, entitled "Xenograft Soft Tissue Implants And Methods Of Making And Using". The '229 provisional application is hereby incorporated by reference in its entirety.

FEDERALLY SPONSORED RESEARCH OR DEVELOPMENT

[Not Applicable]

FIELD OF TECHNOLOGY

The present application is directed to the field of tissue implants and tissue implant processing for transplantation, preferably into humans. The tissue implants are preferably xenograft soft tissue implants, although certain aspects of the present application may apply to bone or hard tissues and to more complex structures such as combined bone or hard tissue implants or even organs from allograft or xenograft sources. The present application provides a chemical process that neutralizes, removes or substantially reduces antigens from and sterilizes and/or strengthens xenograft implants. The present techniques yield soft tissue implants having superior structural, mechanical, and/or biochemical integrity. The present application is also directed to processes for treating xenograft implants comprising soft tissues such as tendons and ligaments, and to implants produced by such processes.

BACKGROUND

When a patient is faced with an orthopedic injury, such as an injury to the Anterior Cruciate Ligament (ACL), the ideal solution to this ailment would be to repair this structure or augment the natural healing process in a way which would re-establish the morphology as it was prior to injury. Unfortunately, ACL repair and regeneration to date has been shown to be unsuccessful primarily due to the lack of healing/regrowth of the native tissues naturally; therefore, total replacement has been the standard of care. Replacement of the ACL via donated human cadaver (i.e. allograft) tendons has proven to be an efficacious option allowing patients to return to their pre-injury quality of life. However, allograft options are burdened with the challenge of depending on a raw material that has large variability and limited availability. Surgeons have tried to mitigate graft variability by limiting donor criteria (e.g. only accepting grafts from donors <45 years of age); however, such limitations have also exacerbated the availability challenge.

Thus, a goal is to find a sufficient pool of donor tissue, with similar genetic, physical and physiological attributes, that could mitigate or eliminate the above problems. This can be done by utilizing xenograft tissue. With a xenograft tissue source donor genetic makeup can be selected and controlled through breeding and herd management, production can be monitored and controlled to ensure the best health and muscle tone, and donor age can be planned and selected. Such donors would thus have exceptional biomechanical structures available for creating high quality grafts which would be recovered from them at their peak age.

Implants comprising soft tissues may be implanted into a recipient to replace and/or repair existing soft tissues. For example, hereditary defects, disease, and/or trauma may damage soft tissues such that replacement and/or repair is desirable. These implants may be allografts, autografts, or xenografts, and the recipients may be human, mammal, or animal recipients. Implants are frequently used where the recipient is a human patient. Implants comprising soft tissues have been used, including in human patients, to replace heart valves, ligaments, tendons and skin, among other tissues.

It is desirable to treat implants, particularly autografts, allografts, and xenografts, to neutralize, remove or substantially reduce one or more undesirable components and/or to instill one or more desirable components. For example, implants may be passivated, or treated to remove or inactivate bacteria, viruses, fungi and other pathogens and antigenic constituents.

Implants comprising soft tissues may be treated with cleaning agents and/or gamma radiation. However, existing techniques suffer from one or more disadvantages. Undesirable results from radiation can include formation of radicals, hydrogen, and low-molecular-weight hydrocarbons; increased unsaturation; discoloration; and oxidation. The use of some chemical sterilizing agents (for example, glutaraldehyde) increases the risk that a toxic response will be evoked. Furthermore, some chemical sterilizing agents (for example, peroxides) may damage the implant, particularly soft tissues, which tend to be somewhat more fragile than bone and hard tissues. A particular concern with the passivation of implants comprising soft tissues is that treated soft tissue may suffer from increased laxity, reduced stiffness, reduced strength, or reduced biocompatibility, which can lead to variable performance of the implant. It is desirable to have treatment processes, including a process for passivation, that does not cause excessive laxity or reduction in stiffness or strength or biocompatibility of the soft tissue.

Gamma irradiation, in order to ensure destruction of pathogens, such as the human immunodeficiency virus (HIV), has been used at doses that result in tissue destruction (e.g. 3.5 Mrad; see, for example, Rasmussen, et al., J. Arthroscopic and Related Surgery, 10(2):188-197, (1994); Goertzen, et al., British Soc. of Bone and Joint Surg., 77:204-211 (805); Loty, et al., International Orthopaedics, 14:237-242, (1990)). Use of ethylene oxide has been found to result in implants that produce inflammatory responses (Kudryk, et al., J. Biomedical Materials, 26:1477-1488, (1992); Thoren, et al., Clin. Orthopaedics, 318:259-263, (1995); Simonian, et al., Clin. Orthopaedics, 302:290-296, (1994); Jackson, et al., Am. J. Sports Medicine, 18:1-9, (1990)). Standard chemical solution treatments, while effective in sterilizing surfaces with which the solutions are brought into contact, tend to be insufficiently penetrating to reach the interstices of tissues, where potentially pathogenic organisms may reside. With regard to sterilization of soft tissue, the potential for damage to the soft tissue by irradiation, ethylene oxide, or chemical solution treatment is of particular concern, because soft tissue are more susceptible to damage than bone tissue. Even milder sterilants such as peroxides may cause damage due to swelling of the tissues and the presence of residual reaction byproducts.

A desirable treatment process includes one or more of the following features: effective removal or inactivation of a wide range of bacterial, viral and fungal pathogens; absence of graft toxicity; retention or improvement of desirable tissue characteristics, such as biomechanical strength or growth-inducing properties; effectiveness across a wide range of operating modifications and/or for a wide variety of tissue types; ability to conclude the process in a final implant tissue container, to ensure sterile packaging and delivery for implantation; ability to apply automated control and monitoring systems and develop an automated and validated process.

A challenge associated with developing a xenograft implant is sufficient removal of foreign xeno-antigens. The presence of such epitopes, specifically Gal$\alpha$1-3Gal_1-4GlcNAc-R (often referred to as alpha-gal) is important to neutralize, remove or substantially reduce due to the human body having antibodies which specifically target this glycoconjugate. Grafts derived from xenographic sources that contain this xeno-antigen are acutely rejected by the human body once implanted.

BRIEF SUMMARY

In one aspect, the present application is directed to a xenograft tissue implant for use in a human patient.

The present application is further directed to a soft tissue implant, preferably for ACL replacement, and preferably designed from xenograft tissue. The xenograft source material is controlled and is free of Bovine Spongiform Encephalopathy (BSE) or other xenograft specific or non-specific disease which might pose a threat to a human recipient. The grafts obtained after treatment are biocompatible in human recipients, with no substantively deleterious immune response or rejection due to xenogeneic antigens. The grafts obtained after treatment are in some embodiments bioactive, with improved healing, remodeling and incorporation.

The present application is additionally directed to processes for making an implant comprising soft tissue more suitable for implantation into a recipient. Soft tissues (such as tendons and ligaments) treated according to the present techniques are wholly or partially passivated by contact with cleaning agents, such as solutions containing any of an oxidizing sterilant (for example, hydrogen peroxide), one or more detergents, saline, carbohydrate, alcohol, acidic or alkali components and/or combinations thereof. The tissues are preferably obtained from xenograft sources for implantation into humans. In some embodiments, the use of at least one carbohydrate (e.g. sugar) treatment step is preferred.

Preferred processes involve an oscillation of pressure in a chamber containing an implant material in the presence of various cleaning solutions, with the optional use of sonication. Specific process steps are implemented to neutralize, remove or substantially reduce xeno-antigens while also enhancing mechanical properties and preferably improving the implant's rate of healing. The resulting implant can be even stronger than the native tissue, has reduced levels of bioburden, and may also have faster incorporation post implantation compared to other available tissue grafts.

In certain embodiments, the processing may occur in an open or closed vessel. For example, certain aspects of the present application may be carried out in whole or in part within a metal, glass or polymeric beaker or basin with a smooth rim for ease of handling tissues and pouring chemicals into and out of the vessel. Certain aspects of the application may also be practiced using a vessel with a threaded or compression fit lid which screws or snaps on to provide closure to prevent spills or contamination during processing, handling, transport or storage of the tissue. Some or all elements of the processing may be carried out with or without pressure cycling, and with or without sonication.

It is contemplated that the tissue may remain in place while various chemicals or chemical solutions are brought into contact by pouring or flowing through the vessel or over or through the tissue, or by addition and removal of solutions or treatment chemicals in either an open or closed vessel, chamber or container. It is contemplated that a vessel may change from open to closed before, during or after one or more processing steps and that pressure cycling, tension and sonication may be applied to or removed from the process before, during or after any one or more pressing steps. It is further contemplated that tissue may be passed through or placed into a solution, then removed from or passed out of that solution and into another solution for the next step in processing.

It is further contemplated that certain embodiments of the present application may be applied to or incorporated along with processing scenarios not requiring or not designed around any particular storage or treatment vessel, processes relying upon flow of treatment chemistries through tissue including bone or hard tissue and tendons or other soft tissues, processes occurring within an open or closed sonication bath, processes for debridement of tissue, and various combinations of the foregoing, such as those taught, for example, in U.S. Pat. Nos. 6,837,907; 6,024,735; 5,977,432; 5,977,034; 5,976,104; 5,820,581; 5,797,871; and 5,556,379 all of which are incorporated herein.

In particular, it is noted that the processing methods of the present application related to controlled xenoantigen removal or reduction may be practiced upon and may be useful for the production of xenografts of multiple tissue types, including soft tissue grafts such as tendons, ligaments, skin, dura matter, fascia, and other connective tissues, and also including hard tissue grafts such as bone and bone derived components such as cortical bone, cancellous bone, demineralized bone matrix, assembled bone grafts and grafts of either naturally occurring or assembled combinations of hard and soft tissue, such as a bone-tendon or bone-tendon-bone implant.

The method of this application provides for implant processing whereby bone marrow, blood, proteins, and particulate matter is efficiently neutralized, removed or substantially reduced, such that what remains is essentially a tissue matrix, passivated tissue matrix, bioinert tissue matrix or bioactive tissue matrix in which a drastic reduction in any form of endogenous material and/or viable organisms is achieved. As described in greater detail below, this is preferably achieved by a process of pressure cycling or oscillation, employing a variety of cleaning and sterilization solutions which are caused to efficiently interpenetrate the matrix. By repeated cycling and changing of the cleaning solutions, the channels of essentially any porous matrix are unclogged, and cleansed. A defined programmed (optionally pre-defined, pre-programmed) cycle of washes is employed, preferably with concurrent sonication (also known as ultrasonic bombardment), to achieve penetrating sterilization of the implant. It is believed that the combination of oscillating fluid pressure and ultrasonic energy accelerates solution interpenetration and endogenous substance removal.

Additionally an osmotic gradient is used during the process, which generates flow in and out of the tissue. This is also referred to as osmotic cycling (transition from hypotonic to hypertonic solutions). This is another method by which bone marrow, blood, proteins, xenoantigens and particulate matter can be efficiently neutralized, removed or substantially reduced.

Preferred processes include the use of kinematic restraint during the cleaning process. The application of kinematic restraint (preferably tension) to the implant while it is contacted with cleaning agents (such as, for example, a detergent, an alcohol, or a peroxide, etc.) can produce more effective cleaning and reduce any damage attributable to the cleaning agents.

Preferred processes can also include a step to increase the final pH of the graft to a level which is basic (pH greater than 7, preferably around 8). While not wishing to be bound by theory, soft tissue grafts that have a basic pH may contribute to enhanced healing of grafts. This is believed to be due at least in part to the fact that basic environments increase osteoblastic activity. It is also contemplated that in some embodiments the step to increase pH is omitted. Graft pH without the added step is between 5 and 7, preferably about 6.

Preferred implants exhibit a controlled reduction in at least one xenoantigen of about 60%, a trypsin digestion less than about 10%, and predicted Ultimate Tensile Force (UTF) based on sorting data of greater than or equal to about 1800N.

In other embodiments, implants exhibit a controlled reduction in at least one xenoantigen of greater than or equal to about 55%, a trypsin digestion less than about 10%, and predicted UTF based on sorting data of greater than or equal to about 2020N.

In some embodiments this application provides a method for production of safe and effective soft tissue (preferably xenograft) implants in an efficient, economical manner. In some embodiments this application provides a method for cleaning, perfusing or passivating implant materials without at the same time compromising the desirable biological properties of the starting implant materials. In some embodiments this application produces implant materials of reduced antigenicity, and preferably implants of enhanced bioactivity.

One embodiment of the present application is a xenograft tendon implant comprising xenograft tendon treated with a sugar solution that exhibits enhanced post-surgical healing and/or strength as compared to either a comparable allograft or autograft implant.

The xenograft implant can be obtained from a number of acceptable xenograft sources. For example, the implant can be of bovine origin. The implant can be taken from a santa gertrudis cow.

The xenograft tendon can be selected from a variety of different tendons present in the body. For example, the implant can comprise an anterior extensor tendon. For example, the implant can comprise an Extensor Digitorum Medialis.

The xeonograt tendon can exhibit an acceptable pH prior to implantation. For example, the implant can exhibit a pH of about 8 prior to implantation. Alternatively, the implant can exhibit a pH of about 8 prior to implantation.

The sugar can be any acceptable sugar. Examples of such sugars include glucose, dextrose, cerelose, aldose, ketose, hemiacetal, pyranose, furanose, erythrose, threose, ribose, arabinose, mannose, allose, altrose, xylose, lyxose, gulose, idose, galactose, talose, sucrose and fructose.

In one embodiment the implant exhibits a controlled reduction in at least one xenoantigen of about 60%, a trypsin digestion less than about 10%, and predicted UTF based on sorting data of greater than or equal to about 1800N. The reduced xenoantigen can be α-Gal. In an alternative embodiment, the implant exhibits a controlled reduction in at least one xenoantigen of greater than or equal to about 55%, a trypsin digestion less than about 10%, and predicted UTF based on sorting data of greater than or equal to about 2020N.

One embodiment of the present application is a method of processing a xenograft tendon comprising: removing a xenoantigen from the tendon, enhancing the strength of the tendon, sterilizing the tendon, chemically rinsing the tendon, optionally decomposing residual peroxide from the tendon and optionally promoting the alkalinity of the tendon. These steps can be carried out in this order or another order.

The method can further comprise one or more steps of specified treatment chemical solution contacting the tendon.

The xenoantigen removal phase or phases can have a Water to Chemical Ratio (WCR) greater than or equal to about 1. The molecular strength enhancement phase or phases can have a Water to Chemical Ratio (WCR) less than about 1. The sterilization phase or phases can have a Water to Chemical Ratio (WCR) less than or equal to about 1. The overall method can have a Water to Chemical Ratio (WCR) of substantially about 0.90.

One embodiment of the present application is a bovine tendon replacement graft comprising a processed anterior extensor tendon recovered from (1) a purebread Santa Gertrudis, Brahman, Angus (i.e. 100% of only one of these), (2) a cross breed with 25% to 100% Santa Gertrudis, Brahman, or Angus ancestry or a combination of these; (3) a cross breed with 50% to 100% Santa Gertrudis, Brahman, or Angus ancestry or a combination of these; or (4) any cross breeds including at least one ancestor selected from Santa Gertrudis, Brahman, or Angus; the graft being recovered from an animal of between about 18 months and about 36 months of age and at least about 200 kg hot standard carcass weight (HSCW) prior to recovery.

The graft can be used for anterior cruciate ligament (ACL) replacement in a human. The graft can he graft has a failure strength greater than an average native human ACL In one embodiment, the anterior extensor tendon can be an Extensor Digitorum Medialis (EDM). In one embodiment, the animal is between about 18 months and about 24 months of age. In one embodiment, the animal is of at least about 295 kg HSCW prior to recovery.

BRIEF DESCRIPTION OF THE SEVERAL VIEWS OF THE DRAWINGS

FIG. 1 shows a calculation method for single strand correlation for sorting tendons.

FIG. 3A shows a bovine tendon produced by the process of the application after implantation in a baboon. FIG. 3B shows an untreated bovine tendon (control). FIG. 3C shows a native ACL for comparison.

FIG. 4A shows a bovine tendon produced by the process of the application after implantation in a baboon (3-month, 40×). FIG. 4B shows a human hamstring autograft for reference (5-month, 200× (Prior Art: Marumo 2005)). FIG. 4C shows the baboon native ACL (40×).

FIGS. 5A-5F show various histologies of the femoral tunnel for comparison. FIG. 5A shows a bovine tendon produced by the process of the application after implantation in a baboon (4×). FIG. 5B shows shows a magnified version of the indicated region (20×). FIG. 3C shows a human autograft at 3 months, 400× (Scranton 1998) for comparison. FIG. 5D shows a bovine tendon produced by the process of the application after implantation in a baboon (10×). FIG. 5E shows a magnified version of the indicated region (40×). FIG. 5F shows a human autograft at 6 weeks, 400× (Scranton 1998) for comparison.

FIG. 6A shows a bovine tendon produced by the process of the application after implantation in a baboon (4×). FIG. 6B shows shows a magnified version of the indicated region (20×). FIG. 6C shows a human autograft at 3 months, 400× (Scranton 1998) for comparison. FIG. 6D shows a bovine tendon produced by the process of the application after implantation in a baboon (4×). FIG. 6E shows a magnified version of the indicated region (40×). FIG. 6F shows a human autograft at 6 weeks, 400× (Scranton 1998) for comparison.

DETAILED DESCRIPTION

Figure 2:
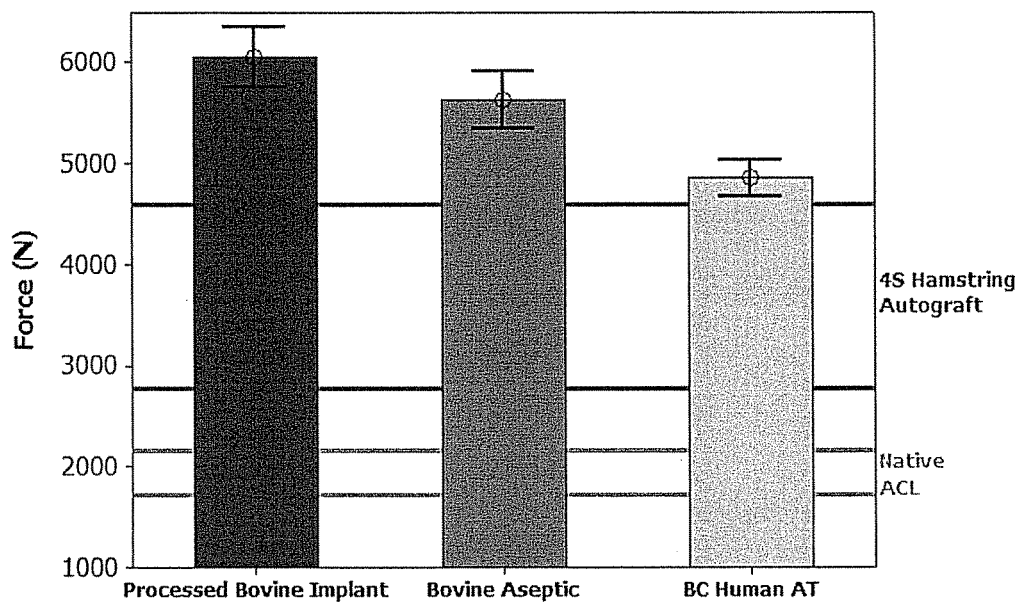
FIG. 2 shows looped implant pull force data. A tendon produced by the process of the application, versus an aseptically treated bovine tendon, versus a comparison human tendon is shown.

In one aspect, the present application is directed to the field of implants comprising soft tissue for use in implantation in humans. The soft tissue implants of the present application are preferably obtained from xenograft sources. This application provides a novel method for processing implant materials including, but not limited to, autograft, allograft or xenograft materials, including bone and soft tissue and preferably soft tissue such as a ligament or tendon. In particular, xenograft soft tissue materials treated according to the method of this application permit grafts to be thoroughly cleaned, machined/shaped/trimmed, sterilized, packaged and then implanted at economies of scale heretofore not possible. Sufficient removal of foreign xenoantigens is performed such that the implants of the present application are not acutely rejected by the human body once implanted. The xenograft soft tissue implants of the present application provide sufficient structural, mechanical, and/or biochemical integrity to use as ACL replacements, for example. These implants have the potential for enhanced mechanical properties and enhanced healing properties (compared to current ACL graft options). The terms "graft" and "implant" are used interchangeably herein.

As used herein, the term "passivate" is intended to refer to the elimination of potentially pathogenic organisms and immunogenic substances from an implant. Thus, both sterility and reduced antigenicity is intended by this term, although elimination of beneficial biological properties of the implant, such as osteogenic properties (osteoconduction or osteoinduction; bone fusion), natural tissue functionality, and desirable structural strength of an implant are not intended by this term. The term "passivation" is preferred to the term "sterilize" because, while sterilization is a goal, that term has an absolute connotation for which the ability to definitively test is limited by the state of the art of making such measurements and/or by the need for attendant tissue destruction. In addition, while the implants produced according to the method of this application may not be completely devoid of any antigenicity or pyrogenicity, these undesirable aspects are greatly reduced, and this too is intended by the term "passivation," as used herein.

As used herein the term "bioinert" is intended to refer to a passivated implant which is not rejected or strongly attacked by the host body.

As used herein the term "bioactive" is intended to refer to an implant or tissue with improved healing, remodeling and/or incorporation which exhibits at least one or more healing or growth phenomena at a higher rate, sooner, with higher quality or with greater robustness than a non-bioactive implant or tissue.

The terms "perfused" or "perfusion," as used herein, are intended to imply efficient interpenetration of cleaning solutions into and through the channels and crevices of materials intended for implantation into a recipient.

As used herein, the terms "rapid" or "rapidly" as they are applied to the process of pressure cycling according to this application mean time frames on the order of seconds to minutes, rather than hours or days.

The terms "sonicate" or "sonication" as used herein means the application of sonic or ultrasonic energy via a container of an implant undergoing processing according to the method of this application under conditions that permit efficient transfer of the sonic energy to the implant. Also called ultrasonic bombardment. Sonic energy may be transferred through a fluid to a workpiece such that efficient cleaning and bacterial or cellular disruption is achieved, without resulting in gross, ultrastructural damage to the workpiece.

"Soft tissue", as used herein, refers to any biological tissue other than bone, including but not limited to tendons, ligaments, fascia, whole joints, dura, skin, pericardia, heart valves, veins, neural tissue, submucosal tissue (e.g. intestinal tissue), and cartilage.

The "soft tissue" described herein is typically a collagenous material that is autograft, allograft or xenograft, preferably xenograft. The soft tissue can be a predetermined length of tendon, a bundle of tendons of the same or different lengths, a predetermined length of ligament, a bundle of ligaments of the same length or different lengths, a segment or segments of pericardium, dermis, fascia, dura, skin, submucosal tissue (e.g., intestinal tissue), cartilage, or a combination thereof. Preferably, the source of the soft tissue is a xenograft tendon.

"Implant" (or "graft"), as used herein, refers to any material the implantation of which into a human or an animal is considered to be beneficial. Accordingly, the implant may be tissue-derived material, such as bone, skin, and the like, or it may be a metallic or synthetic material having an external surface or internal structure that may require cleaning, sterilization or passivation. An implant may comprise autograft tissue, allograft tissue, xenograft tissue or combinations thereof, and in the case of mineralized tissues, such as bone, the implant may comprise mineralized tissue, partially demineralized tissue, completely demineralized tissue, and combinations thereof. The implant may comprise unitary or monolithic graft material, assembled bone materials such as those described in U.S. patent application Ser. Nos. 09/782,594 and 09/941,154, shaped implants such as those described in U.S. Pat. Nos. 6,440,444 and 6,696,073, and allogeneic biocompatible matrices such as those described in U.S. patent application Ser. Nos. 10/754,310 and 10/793,976. The present processes and apparatus may also be employed in the treatment of implants such as those described in U.S. Pat. Nos. D461, 248; 6,290,718; 6,497,726; 6,652,592; 6,685,626; and 6,699,252. All of the foregoing patents and patent applications are incorporated by reference herein.

By definition, a "tendon" is a collagenous cord that attaches muscle to its point of origin, typically to bone. By definition, a "ligament" is a band of collagenous tissue that connects bone or supports viscera. However, such terms are used somewhat interchangeably in the implant art and by recitation of tendon, it is intended to encompass the use of ligament as well.

Although grafts containing only soft tissue are preferred, also included are implants that comprise both soft tissue and bone, such as a bone-tendon-bone graft. A bone-tendon-bone graft comprises one or more bone blocks, and a tendon (or ligament) attached to the one or more bone blocks. Also included are applications of certain aspects of the application to bone or hard tissue grafts. Certain aspects of the application may be further applicable to more complex structures including compound tissues, total joints and organs.

Novel processes are provided for processing implants comprising soft tissue including, but not limited to, bone and soft tissue, mineralized or demineralized tissues and combinations of the foregoing types of tissues. In particular, soft tissue treated according to the present processes permit soft tissue to be thoroughly cleaned, sterilized, and/or passivated, without excessive structural or chemical damage to the soft tissue. Xenograft soft tissue is preferred for its high availability and low cost, although allograft or autograft soft tissue may benefit from processing by the present methods.

The present application provides specific steps to effect removal of foreign xeno-antigens in this novel process for producing xenograft implants that are safe and effective in humans. Grafts derived from xenographic sources that contain foreign epitopes, specifically including but not limited to Gal$\alpha$1-3Gal_1-4GlcNAc-R (often referred to as alpha-gal) are acutely rejected by the human body once implanted. The present inventors have identified that one of the important elements in the controlled removal of alpha-gal (and other foreign epitopes) from a xenograft soft tissue implant is the controlled and focused use of osmotic gradients in processing.

The present inventors have identified that one of the important steps in making a xenograft soft tissue implant viable is the use of at least one carbohydrate treatment step, preferably treatment using a glucose solution. The glucose treatment of the xenograft soft tissue allows for non-enzymatic glycation. While not intended to be bound by theory, it is believed that this glycation produces "stiffening" or "strengthening" of the tissue, which is beneficial in allowing the tissue to retain its mechanical strength and structure throughout the cleaning process. The present inventors have determined that collagen is sensitive to chemical attack at relatively short time durations (~<6 minutes) if a glucose treatment is not performed. In some instances, without glucose and the phenomenon of glycation the tendons may not survive the entirety of the cleaning/passivating process (i.e. lose structural integrity). For exposure duration of this initial glucose step, providing the tissue with at least about 70 minutes of exposure time, and up to 90 minutes or more, is effective at the concentrations used.

Additionally an osmotic gradient is used during the process, which generates flow in and out of the tissue. This is also referred to as osmotic cycling (transition from hypotonic to hypertonic solutions). As a non-limiting example, cleaning solutions can be cycled from DI water, to saline and back to DI water. This can also be expressed as water to chemical ratio (WCR). The WCR is indicative of the overall exposure to DI water within the entire process versus exposure to chemicals or chemical mixtures (including saline). This parameter provides an overall process gradient which is related to xenoantigen removal as well as bioburden removal. WCR values are set at varying levels depending on the intended action for a given set of steps within the overall process. Values on the order of 1.5 to 2 are best utilized to remove unwanted material from the implant. However, this parameter can have deleterious effects on implant structure if set too high. In some embodiments, the preferred settings to balance competing design specifications, within a given processing step, are between 0.60 and 1.05.

Overall exposure to vacuum pressures versus positive pressure may be defined in terms of a Vacuum to Pressure Ratio (VPR), which has also been found to be an important factor for removing unwanted materials within the implant. VPR also has an effect on implant mechanical properties. Values on the order of 4 have the beneficial effect on improving implant strain and ultimate extension (increases) while also protecting against molecular damage of the collagen make-up which would make the implant more susceptible to enzymatic degradation after implantation. However, this parameter can affect the relative efficiency by which unwanted material (i.e. xenoantigens) can be removed from the implant if set too high. In some embodiments, the preferred settings to balance competing design specifications are between 1.90 and 2.40.

In general WCR is calculated as follows:
Overall time within process in which tissue is exposed to DI water only=Water Exposure (min)
Overall time within process in which tissue is exposed to any other chemical or combination of chemicals other than water (saline is considered a chemical for this calculation)=Chemical Exposure (min)
"Water Exposure"/"Chemical Exposure"=WCR This ratio may be calculated for the overall process and also calculated per process step. As used herein, a process step represents a recipe region meant to create a specific design characteristic in the final product. Each process step may consist of or comprise multiple process phases. Each phase consists of a specific chemical solution exposed to the tissue under specified conditions such as contact time, temperature, pressure, vacuum, pressure cycling and sonication.

High WCR indicates more water exposure than chemical exposure within the overall process or within a specific step of a process. For example, a value of 2 would indicate that there is twice as much water exposure than chemical exposure for a given step or for the overall process. It was determined that WCR had a large impact on all factors of interest (e.g. alpha-gal removal, strength, etc.) and was also very sensitive to change. In some cases, significant differences in specifications, yield, etc. could be achieved by changing this parameter by as little as about 0.01 units. This indicates that fluid movement (i.e. osmotic cycling) was very important in the process to achieve desirable implant attributes.

WCR's greatest effect has been observed in relation to alpha-gal removal. At high ratios (e.g., 1.5 to 2.0 or above) it improved alpha-gal removal but higher values can tend to "weaken" the tendon. At low values (e.g., less than 1.0) the likelihood of having a toxic level of residual chemicals is increased. Therefore, overall process WCR has been preferably set at approximately 1.0 for certain embodiments of the present application.

In general VPR is calculated as follows:
Overall time within process in which tissue is exposed to Vacuum=Vacuum Exposure (min)
Overall time within process in which tissue is exposed to Pressure=Pressure Exposure (min)
"Vacuum Exposure"/"Pressure Exposure"=VPR This ratio is also calculated per process step. High values of VPR mean that there is more vacuum exposure than pressure exposure (for the entire run or for specific steps). It was found that this parameter effected mechanical properties but also alpha-gal removal as well.

The foregoing processes may be employed in the cleaning, sterilization and/or passivation of implants comprising soft tissues. The foregoing processes will typically include perfusing the implant with the cleaning agents by cyclically increasing and/or decreasing pressure during the contact of the cleaning agent with the implant, with optional sonication. In addition, an osmotic gradient is used during the process, which generates flow in and out of the tissue. In preferred embodiments, a treatment chamber containing the implant to be treated is filled with the cleaning agent (typically provided as a solution containing the cleaning agent in some concentration). While the implant is immersed in a cleaning agent solution, the pressure in the treatment chamber is cyclically increased and decreased during the contact of the cleaning agent with the implant, with optional concomitant sonication. By cyclically increasing and decreasing pressure, the cleaning agent is made to perfuse into the implant. Deep, penetrating cleaning, sterilization and/or passivation of the implant or portions thereof are achieved by the rate of pressure cycling, the fact of cycling, and the amplitude of pressure cycling, and further by the magnitude of WCR and PVR ratios, the change in these ratios and the sequencing of these ratios within or between phases, within of between steps and throughout the process as a whole. Accordingly, the entire process may be successfully conducted at pressures above or below one atmosphere. Preferably, the entire process is conducted in a chamber which permits for sonication of the contents throughout or at particular stages of the process. In addition, preferably, the entire process is conducted in a programmable system under computer or programmable logic circuit control, so that manual processing is minimized and reproducibility of the process is maximized. Where the processed tissue is any form of allograft or xenograft tissue, election of appropriate solvents has the additional advantage of producing a processed tissue of even lower antigenicity than if such treatment were not included, and in some instances may have additional benefits of enhanced strength, stiffness or other mechanical properties as well as enhanced healing, remodeling or other biological or biochemical properties.

When cycling pressures are employed, the increased pressure may be as high as about 200 pounds per square inch (PSI) above ambient pressure, alternatively about 150 PSI above ambient pressure, alternatively about 100 PSI above ambient pressure, and it may be as low as about 75 PSI above ambient pressure, alternatively about 50 PSI above ambient pressure, alternatively about 25 PSI above ambient pressure, alternatively about 15 PSI above ambient pressure, alternatively about 5 PSI above ambient pressure. Higher pressures may be contemplated by the process, though it is desirable to avoid pressures that would lead to equipment failure or tissue damage due to such pressures. The decreased pressure or vacuum may be as high as about ambient pressure, alternatively about 4 PSI below ambient pressure, or may be as low as about 8 PSI below ambient pressure, alternatively about 12 PSI below ambient pressure, alternatively about 14 PSI below ambient pressure, alternatively about 14.7 PSI below ambient pressure. Any high pressures and low pressures, as specified above, may be combined to define a range of pressures, providing that the minimum selected is equal to or less than the maximum selected. The term ambient pressure applies to either the nominal atmospheric pressure at the location where the process is practiced, or any suitable reference pressure which may be used as a reference for measurement of pressure within the reaction chamber for a given instance of the process. When rapidly cycling increased and decreased pressures are employed, the rate of pressure cycling can be at least about 1 second, alternatively at least about 2 seconds, alternatively at least about 5 seconds, alternatively at least about 10 seconds, alternatively at least about 20 seconds, alternatively at least about 30 seconds, alternatively at least about 50 seconds, alternatively at least about 60 seconds, alternatively at least about 120 seconds, alternatively at least about 180 seconds, alternatively at least about 240 seconds. When rapidly cycling pressures are employed, the rate of pressure cycling can be at most about 5 minutes, alternatively at most about 4 minutes, alternatively at most about 3 minutes, alternatively at most about 2 minutes, alternatively at most about 110 seconds, alternatively at most about 100 seconds, alternatively at most about 90 seconds, alternatively at most about 60 seconds, alternatively at most about 45 seconds, alternatively at most about 30 seconds, alternatively at most about 20 seconds, alternatively at most about 10 seconds. Any maximum and minimum rates, as specified above, may be combined to define a range of rates, providing that the minimum selected is equal to or less than the maximum selected.

Treatment processes may be successfully conducted at pressures above or below one atmosphere. Evacuation pressures between 25 inches of mercury (about 85 kPa or about 12.5 PSI) and the vapor pressure of the solutions in the chamber are adequate. Backfill pressures of between about 40 and 100 PSI (between about 276 kPa and 690 kPa or between about 80 and 200 inches of mercury) are also adequate. The use of rapidly cycling pressures are described in U.S. Pat. Nos. 6,482,584; 6,613,278; and 6,652,818; each of which issued to the present assignee, and each of which is hereby incorporated by reference.

In one embodiment, the entire process is conducted in a treatment chamber which permits for sonication of the contents throughout or at particular stages of the process. In addition, preferably, the entire process is conducted in a programmable system under computer or programmable logic circuit control, so that manual processing is minimized and reproducibility of the process is maximized. After the implant is placed in the treatment chamber, the chamber is filled with a cleaning solution to a level sufficient to immerse the implant in the solution (though some head space can remain in the chamber to facilitate rapid pressure cycling).

The present processes comprise a novel sequence of cleaning agents for treatment of xenograft soft tissue. In preferred embodiments of the present processes, one or more of the cleaning agents are contacted with the implant comprising the soft tissue to neutralize, remove or substantially reduce blood, fat, cells, proteins, antigens, bacterial, viral, fungal or other material. Certain cleaning agents (and methods of using such cleaning agents) are described in U.S. Pat. Nos. 6,482,584; 6,613,278; and 6,652,818, all of which are incorporated herein by reference. Cleaning agents include, but are not limited to, detergents, disinfectants (sometimes called disinfecting agents), decontaminants (sometimes called decontaminating agents), antibiotics, virucidal compounds, and the like. Specialized agents (such as carbohydrates) can be used to enhance tissue properties and/or for tissue protection. Additionally, solutions that are hypertonic or hypotonic can be used to establish osmotic gradients.

The cleaning agents may be provided in the form of solutions or other mixtures. Preferably, the cleaning agent is provided as an aqueous solution (preferably using DI water). For example, one or more of the following cleaning agents can be contacted with an implant comprising a soft tissue:

solutions containing any of an oxidizing sterilant (for example, hydrogen peroxide), one or more detergents, saline, carbohydrate, water-miscible alcohol, such as ethanol or isopropanol, sodium bicarbonate and/or combinations thereof.

Suitable alcohols for use in the present processes include methanol, ethanol, propanol (including isopropanol), and butanol (including isobutanol and tert-butyl alcohol). Isopropanol is presently preferred. The alcohol may be provided in a solution or mixture, with preferred concentrations ranging from about 0.1% to about 100% percent by weight (weight %), alternatively from about 5% to about 95%, alternatively from about 20% to about 90%. Preferred alcohols are those having low molecular weights (for example, in the range of from about 32 g/mole to about 360 g/mole, alternatively alcohols having molecular weights equal to or less than about 61 g/mole, alternatively about 90 g/mole, alternatively about 120 g/mole, alternatively about 240 g/mole, alternatively about 360 g/mole) and/or melting points below the operating conditions of the embodiment being used of the present processes. It is contemplated that other protective agents might be used in place of alcohols, for example polyols. Preferred polyols are those having relatively low molecular weights (for example, in the range of from about 32 g/mole to about 360 g/mole).

Oxidizing sterilants that may be used in the present processes include peroxides, oxides, hypochlorites, percarboxylic acids, and ozone. A preferred peroxide for use in the present processes is hydrogen peroxide. The oxidizing sterilant may be provided in a solution or mixture, with preferred concentration ranging from about 1% to about 15% percent by weight (weight %).

Carbohydrates (or generally "sugars") can be disaccharides or monosaccharides or more complex sugars. For example, those that could be used in the process include, but are not limited to glucose or dextrose or cerelose or aldose or ketose or hemiacetal or pyranose or furanose or erythrose or threose or ribose or arabinose or mannose or allose or altrose or xylose or lyxose or gulose or idose or galactose or talose. Disaccharides (like sucrose or fructose) are also contemplated. Glucose is preferred. The "D" sugars (naturally occurring) as well as "L" are contemplated, "D" configuration preferred.

The carbohydrate may be provided in a solution or mixture, with a preferred concentration ranging from between about 40 and 50 percent by weight (weight %) solution using DI water as a solvent, preferably 45 weight %. Alternative carbohydrate concentrations are contemplated, including lower concentrations such as 20% or 30% and higher concentrations such as 55%, 57%, 60% or 70%. In certain preferred embodiments, supersaturated glucose solutions between about 40 and 50 weight % are preferred. Supersaturated solutions are prepared or result when some condition of a saturated solution is changed, for example increasing temperature, decreasing volume of the saturated liquid (as by evaporation), or increasing pressure.

Saline solutions used in the process include but are not limited to organic and inorganic salt solutions. Examples of inorganic salts are well known and include, but are not limited to, NaCl, NaF, NaBr, KCl, KF, and KBr. Examples of organic salts include but are not limited to sodium acetate ($CH_3COONa$), potassium citrate ($C_6H_5K_3O_7$), ammonium acetate ($NH_4^+CH_3COO^-$), sodium lactate ($NaC_3H_5O_3$) or other salts resulting from the reaction product of an organic acid and an inorganic base. Concentrations of salinity contemplated for use with the present application range from about 0.6% to 35%. Specific embodiments may utilize 27% saline, other embodiments may use 5.9% saline, other embodiments may use 0.7% saline, other embodiments may use 0.9% saline, other embodiments may use 1% saline, other embodiments may use about 6% saline, other embodiments may use 10% saline, other embodiments may use 20% saline.

Sodium bicarbonate or sodium hydrogen carbonate (commonly baking soda; chemical formula $NaHCO_3$) is also used in some embodiments the processes of the present application. Sodium bicarbonate is a white solid that is crystalline but often appears as a fine powder and is soluble in water. It is also commonly referred to as bread soda, cooking soda, and bicarbonate of soda. In colloquial usage, its name is shortened to sodium bicarb, bicarb soda, or simply bicarb.

A detergent solution can be prepared comprising a nonionic detergent, an anionic detergent or both. Nonionic detergents contemplated for use in the process of the application include, but are not limited to, an alcohol ethoxylate, an alkylphenol ethoxylate, an alkyl polyglycoside, a polyoxyethylene ether, a polyoxyethylene sorbitan, or any of the Triton®, Tween® or Brij® series of detergents (e.g. Triton® X-100). Anionic detergents contemplated for use in the process of the application include, but are not limited to, an alkyl benzenesulfonate, an alkyl sulfonate, an alkyl phosphate or an alkyl sulfate, such as the sodium salts of dodecyl sulfate, myristyl sulfate, cetyl sulfate, steryl sulfate and oleyl sulfate (e.g. sodium dodecyl sulfate (SDS; also called SLS)). Triton® X-100 and SDS (SLS) are preferred. Triton® X-100 and SDS have been used for treating bone and soft tissues for a number of years. (See, for example, U.S. Pat. No. 4,801,299). Concentrations used are either about 0.5 or 1 percent by weight (weight %), although other concentrations, for example between about 0.1 to 10 weight % may be used. Detergents can also be mixed with peroxide for more effective cleaning.

Sodium dodecyl sulfate (SDS or NaDS), also known as sodium laurilsulfate or sodium lauryl sulfate (SLS) is an organic compound with the formula $CH_3(CH_2)_{11}OSO_3Na$. It is an anionic surfactant used in many cleaning and hygiene products. The salt is of an organosulfate consisting of a 12-carbon tail attached to a sulfate group, giving the material the amphiphilic properties required of a detergent. Triton X-100 ($C_{14}H_{22}O(C_2H_4O)_n$) is a nonionic surfactant which has a hydrophilic polyethylene oxide chain (on average it has 9.5 ethylene oxide units) and an aromatic hydrocarbon lipophilic or hydrophobic group. The hydrocarbon group is a 4-(1,1,3,3-tetramethylbutyl)-phenyl group. It is related to the Pluronic range of detergents. The pluronics are triblock copolymers of ethylene oxide and propylene oxide. The part formed from ethylene oxide is more hydrophilic than the part from propylene oxide. Triton® X-100 is also a commonly used detergent.

Preferably the specific cleaning agents are hydrogen peroxide, isopropanol, Calimulse® SLS, Triton® X-100 (TNBP), sodium chloride solution, glucose and $NaHCO_3$.

While not being bound to a particular theory it is believed that in some embodiments carbohydrate treatment, preferably glucose, provides molecular strength to the graft. Through non-enzymatic glycation collagen is slightly reacted. This step "ages" the tissue making it more biochemically mature while also protecting it from chemical decomposition in the subsequent steps. Peroxide and detergent, as well as saline treatment, are used for xeno-antigen removal. Through cavitation, chemical decomposition, and an osmotic gradient unwanted antigens and cells are removed from the tissue. Sterilization, through exposure to an oxidizer and detergents, along with cavitation, denatures any foreign bioburden which is subsequently rinsed out of the tissue. Alcohol treatment improves mechanical strength (predominantly increasing stiffness). Chemical rinses (e.g. water) are used to swell tissue in order to remove and dilute residual chemicals left from the previous steps. Optionally, a step to decompose residual peroxide is performed. Baking soda ($NaHCO_3$) can be added in this step in order to actively decompose the super oxide bond of peroxide. Baking soda also increases the final pH of the graft from acidic to basic. Final pH is about 8 in some embodiments, alternatively at least about 7.0, alternatively at least above 7, alternatively at least about 7.5, alternatively at least about 8.5, alternatively at least about 9. While not wishing to be bound by theory, the basic pH of the graft may also contribute to enhanced healing of grafts. This is believed to be due to the fact that basic environments increase osteoblastic activity.

However, it is also contemplated that in some embodiments the above step to increase pH (and/or decompose the super oxide bond of peroxide) is omitted. Graft pH without the added step is between 5 and 7, preferably about 6.

The present processes may include a step or steps where the implant is treated with an agent that is able to increase the surface area of the tissue for processing (e.g. by swelling the tissue). For example, the tissue may be treated with a solution at a desired pH and/or a desired pH may be maintained throughout one or more periods of processing.

Additionally, in accordance with the present techniques, either before, during and/or after a cleaning agent is applied to the soft tissue, the soft tissue is kinematically restrained by tensioning (as described below). A kinematic restraint may be applied as a single restraint or as multiple restraints. The kinematic restraint may be applied in a constant manner or variable manner, for in a steady state or time variable manner.

More particularly, a pressurizable treatment chamber is loaded with the implant comprising soft tissue, optionally a soft tissue to which tension is being applied. It will further be understood that the implant may comprise soft tissue alone or a combination of soft tissue and bone and/or synthetic materials.

A cleaning agent is introduced to the treatment chamber. A sufficient amount of cleaning agent will usually be introduced so as to immerse the implant (in other words, the implant is submerged within the cleaning agent). In the presence of the cleaning agent and optionally with sonication, the cleaning agents are forced into the matrix of the implant using a series of "n" cycles of increased and decreased pressure. The matrix channels of the implant (including the interior of the soft tissue) are repeatedly filled and emptied of cleaning agent and components to be removed as a result of the oscillating pressure. The number of times this step is cycled may be from one to about 150 times (where n=1-150), alternatively from about 10 to about 50 times, alternatively from about 2 to about 30 times).

Suitable temperatures at which the cleaning agent is contacted depend in part on the cleaning agent and its concentration. The transfer temperature is set at 20 C in some embodiments, and no active heating of the fluid is performed. The act of chemical flow/sonication can "heat up" the agents to as high as 39 C. Typically treatment chamber temperatures are between about 27 and 35 C. Higher temperatures (40 C and above) may begin to degrade chemical properties of tissue in some embodiments. For tendon, 50 C or above will begin to degrade the structure of the tissue.

The cleaning agent can be contacted with the implant for a suitable time period in various phases, for example from about 1 minute to about 150 minutes, alternatively from about 4 minutes to about 60 minutes; alternatively from about 60 minutes to about 130 minutes. The foregoing time periods may be consecutive minutes, or they may be partitioned or separated by time periods where the implant is contacted with other cleaning agents, rinsing fluids, or other solutions. Although pressure treatment is preferred and pressure cycling is particularly preferred, it is also contemplated that the present methods may be applied to process tissue at a constant pressure such as ambient pressure, an elevated pressure, or a decreased pressure or vacuum.

As an additional aspect of the present application, processes and apparatus are provided for applying kinematic restraint (including tension, compression or immobilization) to an implant, particularly to an implant comprising a soft tissue such as a tendon. It has been found that when implants comprising soft tissues, such as tendons, bone-tendon-bone grafts, and other soft tissues, are subjected to a treatment process (for example, cleaning, passivation, and/or sterilization that includes contact with one or more cleaning agents, damage to the implant (especially damage to soft tissue) can be reduced by applying tension to the implant (particularly the soft tissues) during at least some portion(s) of the treatment process. By applying a kinematic restraint, such as tension, to soft tissue, damage caused by the treatment process (or one or more of its individual steps) may be reduced, minimized or eliminated. Furthermore, applying tension to the soft tissue can improve the effectiveness and/or consistency of the treatment process.

Conventional processing methods for bone and soft tissue implants include those described, for example, in U.S. Pat. Nos. 5,333,626; 5,512,662; 5,556,428; 5,769,893; 5,797,871; 5,976,104; 6,024,735; 6,293,970, all of which are incorporated herein by reference; as well as other patents and publications. In conventional processes, an implant comprising soft tissue has been subjected to treatment chamber without tensioning of the implant or kinematic restraint of the implant. In such conventional processes, the positioning and orientation of the soft tissue in the process may be altered by cleaning agents, implements or methods used in the processes. This altered positioning or orientation may lead to inconsistencies between different implant specimens, as different implant specimens may have different exposures to the cleaning agents (for example, as a result of overlapping tissues or tissues wrapped around themselves). Also, inconsistent cleaning and access of the cleaning agents to a single tissue may result because one area of the tissue may be overexposed because it is on the outside, and another area of the tissue is balled up, trapped or improperly constrained on the inside receives less exposure to the cleaning agents. Another problem that may arise from the use of conventional sterilization processes with soft tissues, is that the soft tissue may shrivel, leading to an undesirable appearance and structural changes which can later cause excessive post-surgical laxity. Yet another concern in the treatment of soft tissues is excessive post-surgical inflammation. Tissue inflammation may be caused by the interaction of various cleaning agents with blood, fats, or other material inside the soft tissue. For example, the reaction of peroxide with endogenous materials can cause swelling of the tissue and lead to tissue damage. These reactions are commonly referred to as a foaming reaction, as observed in the topical application of peroxide to a surface wound. Remaining byproducts of the peroxide reactions may eventually lead to post-surgical inflammatory response at levels which are detrimental to the healing process. When the tissue is not stretched out (if it is unrestrained during treatment), the foaming reaction may cause more harm, since the foam and byproducts are more likely to be caught inside the tissue.

The present processes may reduce, minimize or eliminate one or more of the foregoing problems. By applying tension to an implant comprising a soft tissue during a treatment process employing cleaning agents, the positioning of the soft tissue in the chamber can be maintained in a desired fashion, and the cleaning agents are unlikely to be applied with enough force to change the positioning. Because cleaning agents contact the implants (particularly the soft tissue) more uniformly and predictably, there will be more consistency between different implants and within a single implant. Soft tissues will have fewer tendencies to shrivel, and as a result there will be less likelihood of generating implants having undesirable appearance. By applying tension to a soft tissue during a treatment process, inflammation and damage from internal foaming reactions can be reduced, because there is greater opportunity for the foaming action to exit the stretched tissue, rather than remain inside the tissue to cause more damage. Additionally, the tension applied during processing will protect the graft from post-surgical laxity which can be caused by shrinkage and shriveling of the graft during conventional processing.

It is desirable to provide an apparatus for applying kinematic restraint that has few parts, is easy to use, and can withstand the chemicals and conditions it will encounter. It is undesirable for the apparatus to have an excessive number of restraints or parts to be actuated. Furthermore, the apparatus should be made from a material that is able to withstand the environments of use and cleaning. For example, it is desirable for the apparatus to be capable of withstanding temperatures in an autoclave which has temperatures in the area of about 120 C. (about 250 F.). In the autoclave, steam should contact and sterilize the various parts of the apparatus. Accordingly, if the apparatus has lots of pieces, screws, tight corners, or little features, it will be less certain that the autoclave will adequately sterilize all those parts of the apparatus, so that it can be used again.

The apparatus for applying kinematic restraint should be designed to expose most or substantially all of the tissue to cleaning agents used in a treatment process. It is generally undesirable for the apparatus to cover significant amounts of the tissue, or restrict the flow of cleaning or rinsing solutions during a treatment process. The apparatus is not only useful during processes for cleaning, passivation, and/or sterilizing an implant, but also may be useful and adapted to provide kinematic restraint to the implant throughout one or more steps of recovery, processing, packaging, shipment, storage, preoperative preparation of the implant, interoperative preparation of the implant, and interoperative handling of the implant.

Accordingly the tissue tensioner should be designed to apply an amount of tension in one or more of the below ranges. The materials used for the tissue tensioner should be strong, biologically inert (in other words, they do not interact with biological tissues) and able to withstand the contemplated chemical and temperature environments for their use and cleaning. Suitable materials for the tissue tensioner include (but are not limited to) polymers, ceramics, and non-corroding metals. Preferred metals include stainless steel, titanium, and alloys such as nickel-based alloys, or materials obtained by plating steel with nickel or chromium. In one preferred embodiment, all parts of the tensioner are made from a suitable inexpensive, sterilizable material, such as stainless steel, or other common sheet metals, or plastics, so that the tensioner might accompany the graft throughout one or more of the steps of processing, packaging, shipment, storage, and preoperative preparation.

When tension is applied to a bovine xenograft tendon soft tissue implant, the amount of tension applied to a tendon is desirably between about 60-75 pounds of force (between about 267 and about 334 Newtons).

A tendon is a tough band of fibrous connective tissue that usually connects muscle to bone and is capable of withstanding tension. Tendons are similar to ligaments and fascia as they are all made of collagen except that ligaments join one bone to another bone, and fasciae connect muscles to other muscles. Tendons are viscoelastic structures and serve as the intermediate to force transmission from a muscle to a bone. When stretched, tendons have a soft tissue mechanical behavior. Several studies have demonstrated that tendons respond to changes in mechanical loading with growth and remodeling processes, much like bones. While not wishing to be bound by theory, it is believed that tension of tendons during treatment allows for processing of the tissue in more of its "natural state" and allows for more effective cleaning as well as preserving its mechanical structure. The amount of tension used is set so that the relaxation over time (while on the tensioner) is minimized. Preferred relaxation amounts are under about 100 N, with under 90 N more preferred and under 50 N preferred. Staying within the above relaxation ranges allows for more effective soft tissue processing.

The present application is preferably directed to a soft tissue implant to be used for ACL replacement designed from bovine tissue. Such an implant will in some embodiments be derived from bovine tendons, preferably tendons from the lower limbs of the animal (extensors). Alternatively, tendons, ligaments or other soft tissues from different anatomical locations and from different animals may be used. For example, the tendons of the head, neck, back or tail from a bovine or other xenograft source. The xenograft soft tissue implant resulting from the treatment processes of the application is stronger than the native tissue, free from bioburden, and may also have faster incorporation post implantation compared to current ACL options.

In certain embodiments, the xenograft soft tissue implants of the present application have the following features:
1. Superior strength: defined to be stronger than human implants derived from the anterior tibialis
2. Biocompatible: defined to be no appreciable deleterious immunological response or rejection due to foreign antigens once implanted
3. Sterile: defined to be sufficient bioburden reduction to prevent an adverse response from recipients In order to ensure that the process is removing "viable" bioburden, 14 day destructive sterile cultures may be performed. This testing gives a level of assurance regarding sterility.

Post-processing, trypsin digestion assays may be performed to measure "biocompatibility". This metric ensures that once the graft is implanted it will not "immediately" (within 1 month) resorb and/or degrade resulting in inadequate strength. This value was derived from a rat study which investigated the resorption of implants with varying trypsin and collagenase digestion values. Values of 30% were found to be highly correlated with unacceptable implant degradation via in vivo mechanisms. Values of 3-5% were found to be correlated with acceptable implant degradation via in vivo mechanisms.

Hydrogen peroxide residual chemical analysis may also be performed post-processing. This metric will ensure that once the graft is implanted it will not have a cytotoxic level of hydrogen peroxide. Previous studies showed that this chemical is toxic to tissues with values >3 ppm failing ISO 10993-5 MEM elution test. However, due to the historical nature of this test producing false positive results when applied to tissue derived grafts, a result of greater than or equal to about 100 ppm may be considered acceptable in some cases.

One characterization of a xenograft implant is determination of removal of foreign xeno-antigens. Foreign epitopes, such as Gal$\alpha$1-3Gal_1-4GlcNAc-R (often referred to as alpha-gal) and others are important to remove, neutralize or substantially reduce due to the human body having antibodies which specifically target these glycoconjugates. Grafts derived from xenographic sources that contain this xeno-antigen are acutely rejected by the human body once implanted. Therefore removal of alpha-gal is measured. A pilot baboon study demonstrated that implants with as low as 60% removal were not rejected. A positive control utilized during this study, which did elicit a massive immune response, had a removal of 40%. For measuring this removal an average of 2 samples from the same processed implant are taken. In one instance, an average removal of alpha-gal greater than or equal to 55% was found to correlate with acceptable graft performance. Note that the removal % represents a relative, not absolute, measure of alpha-gal.

Without wishing to be bound by theory, it is noted that some residual level of alpha-gal may actually be beneficial. If the entities are sufficiently reduced and/or denatured, it is believed that the residual "fragments" of the alpha-gal (or other foreign epitopes) within a xenograft that is meant to reincorporate in a human host can actually enhance healing. Some evidence of enhanced healing (supported by histology) has been seen in the bovine tendon grafts of the present application. A possible explanation for this enhanced/accelerated healing of the xenograft implant is similar to the mode of action of a vaccine (most specifically subunit vaccines). Such vaccines work by exposing the recipient to portions of the infectious bacteria or virus. These portions are typically non-infectious antigens of the relative infectious organism that elicit an immune response without causing the adverse reactions of the disease. It is believed that a similar response is triggered by the bovine tendon implants of the present application. The first phase of the healing cascade after ACL replacement is the "inflammatory" phase (Woo 2000 and Scheffler 1998). It is believed that this phase has been accelerated due to the presence of an "encouraging" antigen, or combination of antigens, whose deleterious effects have been made more benign; however, these antigens are still present to allow a recipient reaction. Therefore, in certain preferred embodiments of this application, the xenograft tendon implant with partially or incompletely removed alpha-gal at some reduced level is believed to be bioactive instead of simply bio-inert.

For ACL replacement, a preferred graft configuration is a looped 2 strand graft. In this configuration, the xenograft implants, regardless of looped diameter (LD) size, will have a 98.6% probability of having a failure strength greater than an average native ACL (native ACL strength=2160 N according to Woo 1991). Data collected by applicants has shown that the average t=0 pull strength of representative xenograft tendon implants of the present application are 6061 N. This value is statistically 1200 N stronger than the largest mean value found in the literature for a 4 strand native hamstring (4590 N According to Hamner 1999). See FIG. 2 and Example 1.

Tendons (or ligaments) are fibrous graft materials that can be difficult to grip. Thus, one of the issues in utilizing a tendon graft is how to fix the tendon upon implantation. One solution that is used is to "bite" the tendon with a component that has some sort of teeth or threads, providing improved gripping over a flat surface. A method for doing so uses an interference screw, which compresses the graft ligament against the wall of the bone tunnel in which it is implanted.

Screws can be made from non-resorbable, bio-compatible materials such as stainless steel, titanium, cobalt chromium-molybdenum alloy or other alloys. Other non-resorbable, bio-compatible materials can be used such as polyamide, polyethylene, polyvinyl alcohol, polyacrylonitrile, polytetrafluorethylene, polyester, and combinations thereof. These screws can also have an eyelet at one end for attaching a suture.

Bioresorbable screws can also be used. Examples of bioresorbable materials include polylactide, poly(L-lactide) (PLLA), poly(D,L-lactide) (PLA), poly(glycolide) (PGA), poly(L-lactide-co-D,L-Lactide) (PLLA/PLA), poly(L-lactide-co-glycolide) (PLA/PGA), poly(glocolide-co-trimethylene carbonate) (PGA/PTMC), polydioxanone (PDS), polycaprolactone (PCL), polyhydroxybutyrate (PHBT), poly(phosphazenes), poly(D,L-lactide-co-caprolactone) (PLA/PCL), poly(glycolide-co-caprolactone) (PGA/PCL), poly(phosphase ester), polyanhydrides, polyvinyl alcohol, hydrophilic polyurethanes, and combinations thereof. Resorbable screws can also be made of biocomposites. A biocomposite material combines a biological ceramic with a bioresorable polymer and changes the resorption and healing profile for the screws. Biological ceramics include tricalcium phosphate and hydroxyapatite.

Another method of fixation is to fix the graft in the bone tunnel with a button and suture. A further method is to use crosspinning, which passes a cross-pin through the tunnel in a perpendicular fashion, and, in some embodiments, the graft is then attached to or looped around the cross-pin. Another method is to pass the graft through the bone tunnel and out the back end and then affix the graft ligament to the outside of the tunnel (with screws and/or washers and/or staples, for example).

Tissue Source/Specification

The present application in some embodiments comprises a soft tissue implant, preferably for ACL replacement, designed from xenograft tissue that would take advantage of current domestication strategies to be able to control the source tissue material. The product includes detailed cattle specifications to ensure consistent raw material. Xenografts can be porcine, ovine, ratite, equine, caiman, bovine or any other suitable animal source. In certain embodiments the xenografts are preferably bovine.

The implants can be derived from bovine tendons, preferably tendons from the lower limbs of the animal (extensors) that have a dense structure throughout the entire length of the tissue. A consistent, reliable source of BSE free bovine tissue is preferred. Preferably, the graft implants are recovered from cattle from Australia or New Zealand. According to the World Organisation for Animal Health (OIE) the country of Australia is free of BSE (Australian Government Dept. of Agriculture, Fisheries and Forestry. DAFF06/4D). Thus, an Australian source is preferred to the relative risk of BSE from cattle born and bred in the United States. Alternate locales could be used in some embodiments as long as such material was confirmed to be BSE free by the OIE or other appropriate authority, and structurally equivalent or suitable. Tendons are recovered from cow limbs. For ACL replacement, in some embodiments the preferable bovine tendons for use in humans are as follows:

Extensor Digitorum Lateralis (EDL)
Extensor Digitorum Communis (EDC)
Extensor Digitorum Medialis (EDM)

Each of these tendons are anterior extensors that have sufficient length to be used as ACL replacement grafts. Each of the four legs from a cow contains these 3 tendons (the tendons from the front limb being cut somewhat short due to typical slaughtering techniques). Tissue is preferably free from nicks, cuts, or tears. Significant removal of outer connective tissue attached to tendon is preferably performed. A preferred minimum length of 260 mm is desired in the raw material in some embodiments. This preferred minimum length takes into account the length needed for tensioning during processing, and then producing a looped implant of at least 80 mm. Other tendons can be contemplated for use as long as the length requirements are met.

Tendons are preferably used that have consistent strength and quality throughout their length, preferably bovine Extensor Digitorum Medialis (EDM). Prior to processing, tendons may be stored at reduced temperatures. Certain cattle breeds have been found to have preferably long and strong tendons. These include preferably (1) a purebread Santa Gertrudis, Brahman, Angus (i.e. 100% of only one of these), (2) a cross breed with 25% to 100% Santa Gertrudis, Brahman, or Angus ancestry or a combination of these; (3) a cross breed with 50% to 100% Santa Gertrudis, Brahman, or Angus ancestry or a combination of these; or (4) any cross breeds including at least one ancestor selected from Santa Gertrudis, Brahman, or Angus. To achieve best relative strength and maturity of tendons, animal weight (hot standard carcass weight, HSCW) is preferably greater than or equal to about 295 kg. However, HSCW of cattle can be less than or equal to about 266 kg and as low as about 200 kg in certain embodiments.

In order to secure higher yields after processing and to ensure less variability in mechanical strength from implant to implant, a correlation was developed between raw tissue implant parameters and Ultimate Tensile Force (UTF). A predicted UTF of 2020N was found to be desirable in some embodiments. In other embodiments, any value greater than 1800 N may be desirable, and any value over 1725 N may be acceptable. It has been reported that any value above 1000 N may be clinically acceptable due to the presumed loading of the native human ACL during strenuous activity, and any value greater than 445 N may be clinically acceptable due to the presumed loading under normal activities of daily living. (Noyes 1976)

Specifically in reference to bovine, tendons from older cows (e.g., those aged more than about 18 months) are desirable because they are typically larger (greater cross-sectional area (CSA) and more mature (better structural integrity). However the incidence of BSE has been found to be more prevalent in "older" cows so this must be balanced. In some embodiments, animals of at least about twelve months age may be acceptable, preferably at least about 18 months of age, alternatively between about 18 and 24 months, alternatively between about 18 and 36 months, alternatively between about 24 and 30 months, alternatively between about 30 and 36 months, alternatively greater than 36 months. It is known in animal husbandry that age of animals may be determined by analysis of the development of the animal's teeth along with other factors. For instance, a cow of less than 18 months age might be found to have no permanent incisor teeth, while a cow of up to 30 months age might be found to have no more than 2 permanent incisor teeth. Cows up to 36 months might be found to have as many as 4 permanent incisor teeth. Thus, cow acceptability can be measured by tooth presence. In some embodiments, cows are acceptable that have between 2 and 4 permanent incisor teeth.

As for animal weight, specifications are determined based on historical yield. A preferred tendon yield at sorting is about 80%. This means that 80% of the raw tendons received have acceptable dimensions to produce a tendon with a single strand UTF of 2020 N or greater. Cow weights less than about 295 kg may decrease the yield considerably. Single strand correlation formula for sorting is shown in FIG. 1. Among the many challenges in working with biological materials is the potential for variance in material properties due to factors such as fluid content, and heterogeneity of fiber structure, for example. To account for these variances, certain embodiments of the correlation may include factors such as a Looped Diameter, Width and Thickness which are more than simple gross measurements of the tissue morphology, as depicted in FIG. 1. The major (width) and minor (thickness) dimensions were measured at 6 points along the length of the tendon. The loop diameter (LD) was also measured using a standard tendon sizing block. Definition of tendon shape includes a major average of 6 measurements from the major axis and a minor average of 6 measurements from the minor axis. Major axis measurements were preferably made with calipers and minor axis measurements were preferably made with a drop gage (weight applied about 200-215 grams).

EXAMPLES

Example 1

In one embodiment the graft utilizes a bovine tendon source, recovered from Australian cattle, that has a dense structure throughout the entire length of the implant. Xenograft implants are produced that preferably are between 8.0 and 11.5 mm looped diameter (LD) sizes and have an average length of about 270 mm. The table below (Table 1) summarizes other relevant dimensional characteristics for these grafts.

TABLE 1

| Width (mm) | Thickness (mm) | CSA (mm2) |
|---|---|---|
| 9.0 ± 1.3 * | 3.2 ± 0.58 * | 27.7 ± 4.1 * |

* The ± ranges represent standard deviation.

Example 2: Looped Implant—Pull Force Data

As shown in FIG. 2, a bovine implant of the instant application shows about a 1200 N greater pull force than a "High" Mean Autograft (p-value<0.01). The calculated probability of the xenograft being stronger than Native ACL is 98.6% (References for human: Hamner (1999), Conner (2008): 4-Strand Hamstring; also Woo 1991 and Noyes 1976). This data illustrates an enhanced feature of the bovine tendon ACL implants of the instant application. The plot compares implant strength, measured in Newtons, to native bovine tendons (unprocessed), processed allograft human tendons, and values found in the literature. The 4 strand (4S) hamstring data are average values for such grafts found in Hamner (larger value) and Connor (smaller value). The native ACL data was found from Woo (larger value) and Noyes (smaller value). A statistical analysis was done in order to compare the processed bovine data to the larger average 4S hamstring data found in Hamner. Statistically the bovine implant is 1200N stronger than an average 4S hamstring. Note: the bovine implant, unprocessed bovine tendon (Bovine Aseptic) and the BC Human AT (anterior tibialis) were all tested as 2 strand (looped) grafts using the same test method. The 4S hamstrings measured by Hamner were tested as a double bundle (2 looped tendons) using a test method similar to how the other tendons were tested. It is unclear what the specific test method was to test the ACL tendons measured by Woo 1991 and Noyes 1976. It is clear that Woo's method included bone attachments and tested the ACL as naturally found within the knee.

The probability statement given is a Reliability Analysis that was done using a Weibull Analysis Methodology. Such an analysis scheme is commonly used in order to determine the reliability of automobile components, airplane components, and other medical devices such as coronary stents, angioplasty balloons, and neurovascular embolic coils. The probability of 98.6% is a statistical value determined from strength data and has a level of statistical confidence of 95%. In laymen's terms it gives the relative "chance" that any given bovine implant (processed and prepared using current methods) will be mechanically superior to a native ACL (according to Woo 1991). Utilizing the current processing and screening methods for creating these implants, this value verifies the strength to be 2160N. The chance of any given implant having strength below this value is 1.4%. Note: probability should not be confused with occurrence. This value does not mean that 1.4% of all tendons produced will be weaker than a native ACL implant. This value is similar in kind to the chance of rain that is predicted daily by the weather man. If the chance of rain is 1.4% it is fairly certain that it will not rain. The number of times that it actually has rained when the chance of rain was 1.4% would be the occurrence and is a different statistic calculated differently. In the realm of device manufacturing this occurrence is associated with the yield of a product.

Example 3—Animal Study

In order to ensure that hyper acute rejection is prevented when implanting xenograft ACL implants of the present application, a 3 month animal study in primates (specifically baboons) was performed. This choice in animal model was due to its immunological similarity to humans. Only old world monkeys (i.e. baboons, macaques, and rhesus monkeys) and anthropoid apes (i.e. chimpanzees and gorillas) have the same anti-alpha-gal antibody that humans possess. In general, this study proved the superior properties of the xenograft implants of the present application. No acute rejection of the processed grafts was seen, most immunological blood chemistries returned to normal at 3 months and implant healing was significant and unexpected (in magnitude and rapidity).

In this study five baboons were implanted with bovine derived ACL implants processed by the method of this application. One baboon was implanted with an unprocessed bovine derived implant which was treated with antibiotics only (positive control meant to elicit a hyper-acute response). Such a treatment was performed on the positive control in order to prevent any immunological response that could be attributed to microscopic organisms that may have been introduced during tendon recovery. In order to be "cleared" for implantation a sample from all implants, including the untreated positive control, had to pass a 14 day sterility culture. ACL replacement that was performed on the baboons involved using a "open knee" technique. Note the baboon knee is approximately 30 to 40 mm wide (medial to lateral measurement of the tibial plateau). In comparison a human knee is 80 to 100 mm wide.

Tendons were treated through the process of the instant application and then selected for implantation with the best possible combinations of the following parameters (as described above). Final implants: highest α-Gal removal (>60%), trypsin digestion less than 10%, and highest predicted UTF based on sorting data (>1800N).

Baboons were cared for in an AAALAC-accredited facility and all procedures were approved by the facility's Institutional Animal Care and Use Committee (IACUC). The six baboons were single-housed in aluminum cages for the duration of the study. A complete physical exam was performed on each baboon prior to study initiation. Minor dental disease in all baboons was the only significant finding in these otherwise normal females. Body weights were obtained at physical exam and various time points throughout the study.

All animals were sacrificed at 3 months. The primary outcome of the study was the histopathological assessment of each implant in comparison to the contralateral limb's ACL (negative control) and the positive control. Throughout the study immunological blood serologies were also assessed at 2, 4, 8, and 12 weeks in order to have a sense of how the implant may be affecting the recipient systemically during the study period.

The systemic immune response of each animal was evaluated using 4 immunological assays (Table 2). Each of these assays was carried out using blood/serum samples received for each baboon at pre-surgery, 2 weeks post-surgery, 4 weeks, 8 weeks, and 12 weeks. In each of these assays, increases or elevated levels indicate an immune response to the implant; a return to baseline as quickly as possible is ideal.

Table 2: Various immunological assays used in this study to evaluate the overall systemic immune response of the baboons to a bovine ACL implant. In all assays, lower results indicate a less severe reaction.

TABLE 2

| Assay | Purpose |
|---|---|
| Serum anti-α-Gal ELISA | Evaluation of changes in anti-α-Gal production over the time course of the study. |
| Total IgG & IgM | Evaluation of total immunoglobulin production over the time course of the study |
| Antibody mediated complement dependent cytotoxicity | Determination of the severity of the antibody reaction to bovine cells by measuring cell kill |
| Mixed lymphocyte reaction (MLR) | Evaluation of the cell-mediated ability to recognize foreign antigens as a response to transplantation. |

Serum Anti-α-Gal ELISA

Anti-α-Gal is an immunoglobulin that is produced in response to exposure to the α-Gal epitope, thought to be the primary cause of acute rejection of Xenograft implants. Serum levels of anti-α-Gal IgG were evaluated using standard ELISA techniques. The assay used BSA-α-Gal as the solid phase for immobilization of anti-α-Gal IgG. Horseradish peroxidase (HRP) conjugated rabbit anti-human IgG secondary was used for detection of the anti-α-Gal primary antibody. A chromogenic substrate was used to degrade the HRP and generate a color. A stop solution was added after incubation with the chromagen and the absorbance values at 492 nm were determined. From these results, the anti-α-Gal titer was calculated. The titer level of anti-α-Gal was defined as the reciprocal of the serum dilution that yielded 50% of the maximum OD (maximum binding). Results were calculated in the form of fold-increase in anti-Gal antibody level at each time point over pre-surgery levels.

Total IgG and IgM Antibody Levels

Serum levels of total IgG and IgM were determined using ELISA methods to indicate the extent of the immune response to all bovine antigens, including anti-α-Gal and non-Gal antigen responses. Briefly, these assays used goat anti-monkey IgG or IgM antibody for solid phase (microtiter wells) immobilization and horseradish peroxidase (HRP) conjugated goat anti-monkey IgG antibodies for detection. Both capture and detection antibodies were cross-absorbed on monkey IgM (or IgG) and IgA agarose columns, thereby ensuring specificity for IgG (or IgM). After exposure to a chromogenic substrate and subsequent stop solution, the absorbance values at 450 nm were determined. The concentration of antibody is proportional to the absorbance and was calculated from a standard curve. Results were reported as raw values (mg/mL).

Antibody-Mediated Complement-Dependent Cytotoxicity

This assay was used to indicate to what extent the antibodies produced were killing bovine cells. In brief, bovine peripheral blood mononuclear cells (PMBCs) were isolated and adjusted to a known concentration. Serially diluted samples of baboon serum were exposed to bovine PBMCs and incubated, followed by the addition of rabbit complement. After incubation, cells were stained with fluorescein diacetate and propidium iodide. Live cells (stained green) and dead cells (stained red) were counted using flow cytometry. The SLU50, defined as the serum dilution that kills 50% of target cells (bovine PMBCs), was determined from these data. These results are presented as fold-increase of the SLU50 over pre-implantation levels. Higher levels of cytotoxicity indicate a more intense response to bovine antigens (i.e. a more active complement reaction).

Mixed Lymphocyte Reaction (MLR)

This assay was used to indicate if there was a cellular response to the bovine implant, independent of antibody production. Baboon and bovine PMBCs were isolated from fresh whole blood. Bovine cells (used for determining xenogeneic response) and a portion of the baboon cells (used for allogeneic and autogeneic responses) were treated with Mitomycin C to render them unable to proliferate. Responder cells (baboon PMBCs) were incubated with stimulator cells (Mitomycin C treated autogeneic, allogeneic, or xenogeneic cells) or a positive control (phytohemagglutinin-M or PHA-M) for 5 days. Cellular proliferation resulting from exposure to the stimulator cells was quantified using an ELISA kit. The stimulation index for each baboon and each stimulator cell type was calculated by normalizing the stimulated proliferation by the normal, non-stimulated baboon PBMC proliferation. Greater stimulation index indicated increased proliferation of baboon PBMC and therefore a greater incompatibility of the responder cell and stimulator cell sources.

Results

Serum Anti-α-Gal ELISA

The anti-α-Gal ELISA was used to measure systemic levels (titer) of anti-α-Gal production compared to baseline levels. Results of this assay are reported in fold-increase in titer level over pre-implantation levels. Two animals had undetectable levels of serum anti-α-Gal in the baseline serum samples; the average of all other animals' baseline values was used for analysis of fold-increase for these 2 animals for the duration of the study. It is unknown whether these animals actually had an extremely low circulating serum anti-α-Gal level or if there was a problem with these serum samples from this time point.

Over the course of the study, all animals experienced a peak in anti-α-Gal production by 2 weeks post-implantation. After the 2 week time point, serum anti-α-Gal levels dropped at each time point for all treated animals for the remainder of the study. It was expected that the animal that experienced a post-surgical infection (DC12) would have elevated levels of immunoglobulins; however it is interesting that the anti-α-Gal specific IgG would also appear elevated over the course of the study compared to other animals. It is unknown how much of the large increase in titer level was due to the infection, which likely increased recruitment of cells and antibodies that result, and how much it was related specifically to the tendon itself. However, it appears based on the trend over the last half of the study that this animal would return to baseline levels at longer time points.

The only animal that exhibited a plateau in serum anti-α-Gal level at any point in the study was the positive control between 4 and 8 weeks. It was anticipated that this animal should have had elevated levels of anti-α-Gal since the implant contained more residual α-Gal compared to all other implants, though the serum anti-α-Gal levels were comparable to other animals at each time point. At the conclusion of the study, the reduction in fold increase for this animal appeared to be slowing down compared to all other uncomplicated animals, which demonstrated titer fold-increases of less than 10-fold by this point. It is possible that since this implant had some reduction in α-Gal that the expected differences in the serum anti-α-Gal results between the positive control and treated implants was delayed and that longer time points may have begun to show more pronounced differences as the treated animals continued to exhibit more pronounced drop in anti-α-Gal by comparison.

Total IgG and IgM Antibody

With the exception of the positive control animal, all animals experienced peak IgG levels at 2 weeks post-surgery, coinciding with the peak in anti-α-Gal. All uncomplicated treated animals had peak IgG just outside the normal range for this antibody (within 6 mg/mL of the upper limit), indicating that the antibody response was not severe. The positive control animal, however, peaked at the endpoint of the study and at a higher level than all other uncomplicated animals, indicating a potentially continued and increasing response to the implant. All animals receiving treated implants returned to normal or near-normal levels by the endpoint of the study except for an animal with an initial post-surgical infection whose IgG levels remained elevated over the 12 weeks of the study despite the resolution of the infection.

Unlike total IgG levels, IgM levels remained relatively flat over the entire 12 week study period and were within normal ranges for all animals. Though levels remained within the normal range, the peak IgM levels occurred within the 2-4 week time points for the study for all treated animals, while the positive control animal did not experience the peak IgM level until the 12 week endpoint.

Since IgM is the first responder to foreign antigens in the body, it was expected that these levels may peak above average levels at the early time points in the study. However, the coinciding peak in IgG levels at these times points with the relatively flat IgM levels indicates possible antibody isotype switching, with IgM switching to IgG isotype during the study. IgG is typically involved in the secondary immune response and plays an important role in activating the complement cascade and antigen removal. The isotype switch from IgM to IgG suggests that once the implants were recognized as foreign, the increase in IgG resulting from the switch would be beneficial in faster removal of foreign material.

Antibody-Mediated Complement-Dependent Cytotoxicity

All animals exhibited a peak in SLU503 (SLU50=serum lytic unit 50=the serum dilution that kills 50% of target cells (bovine peripheral blood mononuclear cells)) at 2 weeks post implantation, indicating that the most cell kill occurred as a result of antibody production at this time point. This is not unexpected, as the antibody levels for both IgG and IgM peaked around this time point as well. All animals returned to baseline or near-baseline levels by 8 weeks post-implantation and maintained that level for the remainder of the study. It is interesting, however, that the SLU50 for the positive control animal remained relatively flat over the entire time course of the study compared to all treated animals. It is possible that since the IgG level for this animal was beginning to peak at the 12 week time point that longer time points may have begun to show more of a reaction in the assay.

Mixed Lymphocyte Reaction

The MLR assay was used as a measure of the cellular response to the tendon implant over the course of the study. This assay measures the increased proliferation of baboon lymphocytes cells resulting from exposure to stimulator cells (antigenic cells such as allograft or xenograft); increased proliferation of baboon lymphocytes indicates a greater incompatibility with the stimulator cell. The baboon lymphocyte proliferation is reported as the stimulation index, defined as the stimulated proliferation normalized by the non-stimulated proliferation; a stimulation index of 1 indicates no increase in stimulation resulting from stimulator cells. Increased stimulation index indicates an increased cellular response and greater incompatibility. Phytohemagglutinin (PHA) was used as a positive control for the assay, as this is a known lymphocyte stimulator.

All treated animals exhibited peak xenograft stimulation indices at 4 weeks post-implantation with the exception of one animal whose stimulation index remained relatively flat over the entire study. In comparison, the positive control animal did not exhibit peak response until the 8 week time point. By 12 weeks, 50% of the animals' xenograft stimulation indices return to baseline levels while the remaining 50% showed slight increases at 12 weeks, though not as high as the peak values at 4 weeks.

All animals exhibited xenograft stimulation indices below the average PHA positive control stimulation index through 4 weeks. At the 8 week time point, the positive control animal and 1 treated animal exhibited xenograft stimulation indices higher than the PHA control. By 12 weeks, 2 treated animals had stimulation indices at or above the PHA control while the positive control animal returned to near baseline. This may indicate that the two treated animals (having stimulation indices at or above the PHA control) had increasing cellular activity at these time points while the cellular activity of all other animals, including the positive control were subsiding.

For comparison to the xenograft response, allograft stimulation was also evaluated in the assay. In general, allograft stimulation indices were higher than or comparable to xenograft stimulation indices over the course of the study, which may be attributed to major histocompatibility complexes (MHCs) in the pooled allogeneic baboon cells. This may indicate that the cellular response to the implants may not be xenograft specific, but rather a response to any foreign material seen as immunogenic by the responder cells. Since the results of the MLR assay are based on cellular response, it is possible that the peak in MLR stimulation index between 4-8 weeks corresponds to the cellular influx related to the inflammation and proliferative phases of the healing cascade.

Histological Results are Shown in FIGS. 3-6

Figure 3C:
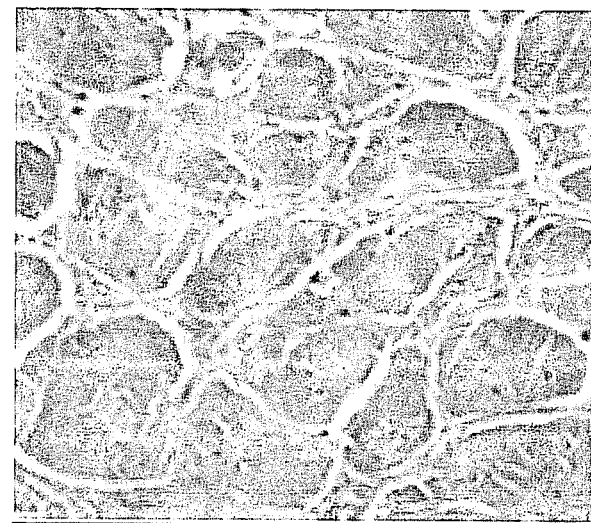
FIGS. 3A-3C show various histologies for 3 month necropsy, 40×.
Figure 3B:
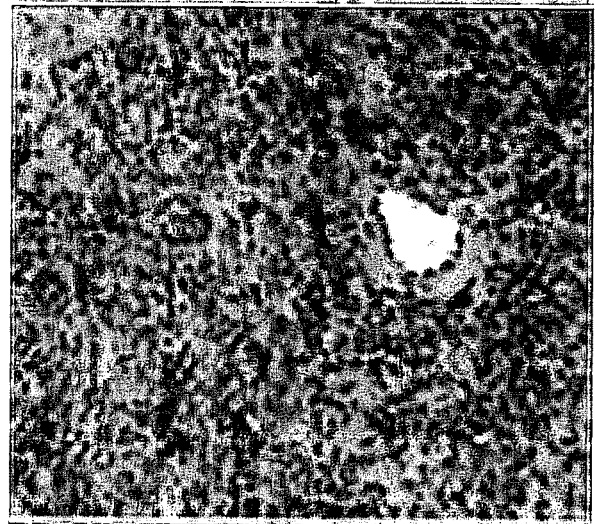
Figure 3A:
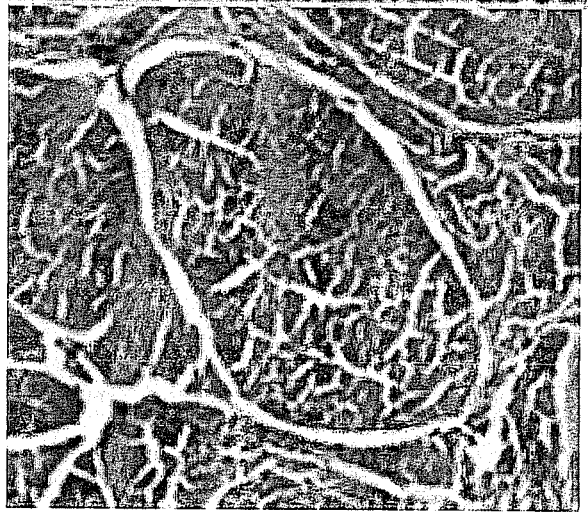

FIG. 3 shows a comparison of the mid-substance histological results from the animal study. Each picture in this slide is an H&E (hematoxylin and eosin) stained histological section. All sections are taken in the transverse (radial, looking down at a cross-section of the implant) direction. The left most (FIG. 3A) and right most (FIG. 3C) pictures are from the same animal. The right most is from the middle of the animals left leg native ACL. The left most is from the middle of the animals right leg whose ACL was replaced with a bovine implant.

The middle picture (FIG. 3B) is from a different animal that received a bovine implant that had not been processed (positive control). This positive control was implanted in order to get a notion of what hyper acute rejection looked like. The middle picture (positive control) demonstrates rejection of the graft. The cells that can be visualized are giant cells, eosinophils, and lymphoid cells. These cells may be considered to be "attacking/destroying" the implant tissue.

However, as can be seen in the left most and right most pictures, the processed bovine tendon implant of the instant application has a strong histological similarity to the native ACL of the same animal. This illustrates surprisingly efficient healing.

Figures 4A, 4B, 4C:
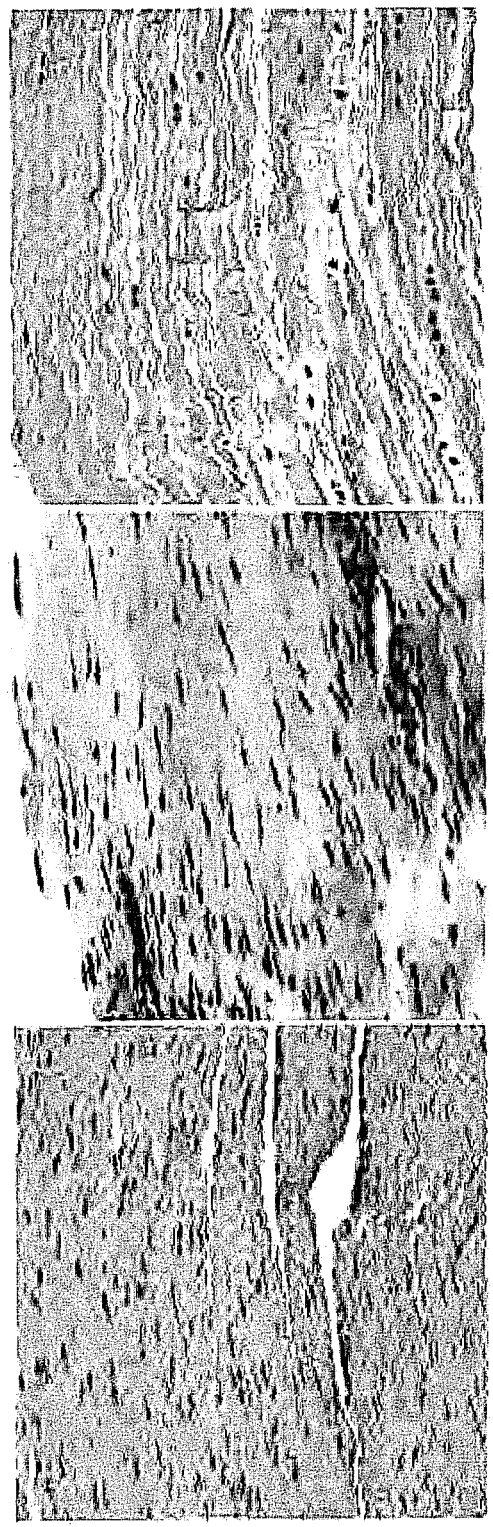
FIGS. 4A-4C show comparisons of various histologies.
Figure 6A:
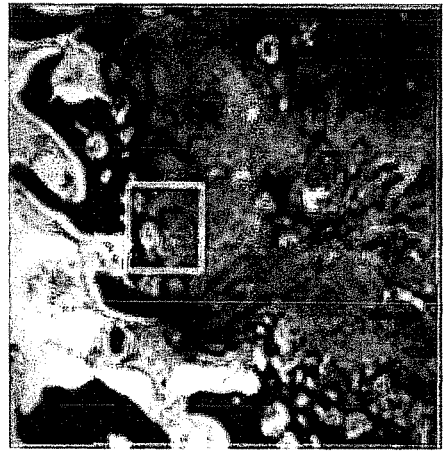
FIGS. 6A-6F show various histologies of the tibial tunnel for comparison.
Figure 6B:
Figure 6C:
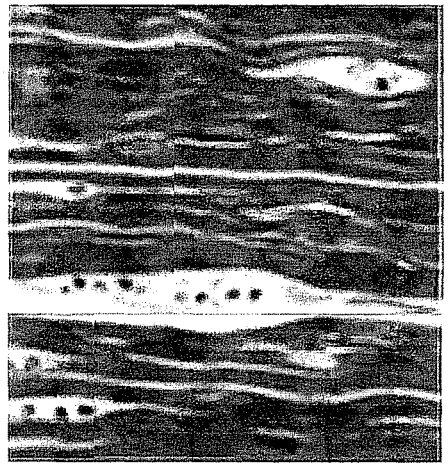
Figure 6D:
Figure 6E:
Figure 6F:

FIG. 4 shows another mid-substance histological comparison. Again, the left most (FIG. 4A) and right most (FIG. 4C) pictures are from the same animal. These pictures are also H&E (hematoxylin and eosin) stained histologies. These sections were taken in the longitudinal direction (along the long axis of the implant/ligament, the individual fibrils (small bundles of collagen) can be visualized).

The middle slide (FIG. 4C) is a longitudinal section of a human hamstring autograft that was retrieved from the literature. As can be seen there are great similarities between each of the three sections shown in this slide. This also illustrates surprisingly efficient healing and also the similarities of the xenografts of the present application and traditional autograft.

FIG. 5 shows radial sections taken within the femoral tunnel that was created to hold the graft in place within the femur. All pictures on this slide are sections stained with Masson's Trichrome. The right most slides (FIG. 5C and FIG. 5F) were taken from literature and depict certain desirable cells/structures that indicate good incorporation/transition of the implant into the surrounding bone. As can be seen there was evidence of chondrocytes (FIG. 5A and FIG. 5B) and Sharpey's like fibers (FIG. 5D and FIG. 5E) in the femoral tunnel of the animals that received processed bovine implants. This depicts certain desirable cells/structures that indicate good incorporation/transition of the implant into the surrounding bone.

FIG. 6 shows radial sections taken within the tibial tunnel that was created to hold the graft in place within the tibia. All pictures on this slide are sections stained with Masson's Trichrome. The right most slides (FIG. 6C and FIG. 6F) were taken from literature and depict certain desirable cells/structures that indicate good incorporation/transition of the implant into the surrounding bone. As can be seen there was evidence of chondrocytes (FIG. 6A and FIG. 6B) and Sharpey's like fibers (FIG. 6D and FIG. 6E) in the tibial tunnel of the animals that received processed bovine implants. This depicts certain desirable cells/structures that indicate good incorporation/transition of the implant into the surrounding bone.

CONCLUSIONS

The serum anti-α-Gal titers appear to correlate with the level of α-Gal removal achieved from the tendon implants despite the small sample size of the study. While the rest of the immunological assays did not have a strong correlation with the histological results (except serum anti-α-Gal discussed above) they did provide for some level of monitoring of the animals over the time course of the study. Also these results do imply that a return to baseline or near-baseline levels for these markers by 12 weeks post-surgery is a positive outcome, as nearly all treated animals were at or near-baseline levels for nearly all immunological tests. Furthermore, these results indicate that peak levels experienced in these assays are not detrimental to the implant over the duration of this study and established the time course for the immunological responses to a xenograft ACL implant.

In general, histological findings from the midsubstance and tibial tunnel locations revealed no inflammation to the occasional mild inflammatory response. The femoral tunnel locations revealed more evidence of an inflammatory response, though in the use of an interference screw for fixation in the femoral tunnel could be causing compression damage and can account for some of the increased inflammation in these regions. In contrast, the positive control animal exhibited classic signs of acute rejection in both tunnel locations and to a somewhat lesser extent in the midsubstance of the graft.

An unexpected result of the study was the level of remodeling/healing that was evident at the 12 week end point of the study. Though some degree of remodeling was expected, fibrocartilage formation, graft/tunnel incorporation, ligamentization, and the formation of Sharpey's fibers was evident to large a degree in the tibial tunnels of all treated implant animals. Many animals showed excellent incorporation at or near 360° around the tunnel/implant interface. The midsubstance of all treated implants displayed evidence of ligamentization and neovascularization with little to no inflammatory response. The results in the femoral tunnels were less impressive in terms of remodeling, but the histological findings were still promising with evidence of fibrocartilage formation and graft/tunnel incorporation, though to a lesser extent than in the tibial tunnels. Interference screw fixation in the femoral tunnel may have played some role in the somewhat slower remodeling and supports the use of current suspension fixation systems in the femoral tunnel. In comparison, the positive control animal revealed little to no evidence of remodeling and was instead being destroyed by acute rejection response.

Overall, the results of this study were highly positive indicators that a bovine tendon processed using the methods of the present application is rendered sufficiently less immunogenic to prevent acute rejection of the implant. The level of healing of the implant was better than anticipated. It is possible that either the small increase in tissue digestibility resulting from the methods of the present application or the low level of residual xeno-antigens left in the tendons induced a quicker response to the implant and resulted in faster healing.

All patents, test procedures, and other documents cited herein, including priority documents, are fully incorporated by reference to the extent such disclosure is not inconsistent with this application and for all jurisdictions in which such incorporation is permitted.

BIBLIOGRAPHY

Conner et al. Tensioning of Anterior Cruciate Ligament Hamstring Grafts: Comparing Equal Tension Versus Equal Stress. Arthroscopy. 2008 December; 24(12): 1323-1329.

Hamner et al. Hamstring Tendon Grafts for Reconstruction of the Anterior Cruciate Ligament Biomechanical Evaluation of the Use of Multiple Strands and Tensioning Techniques. The Journal of Bone & Joint Surgery. 1999; 81:549-57.

Marumo et al. The "ligamentization" process in human anterior cruciate ligament reconstruction with autogenous patellar and hamstring tendons: a biochemical study. Am J Sports Med. 2005 August; 33(8):1166-73. (Epub 2005 Jul. 6).

Noyes et al. Biomechanical analysis of human ligament grafts used in knee-ligament repairs and reconstructions. J Bone Joint Surg Am. 1984; 66:344-352.

Noyes et al. The strength of the anterior cruciate ligament in humans and Rhesus monkeys. J Bone Joint Surg Am. 1976; 58:1074-1082.

Scheffler et al. Graft remodeling and ligamentization after cruciate ligament reconstruction. Knee Surg Sports Traumatol Arthrosc. 2008 September; 16(9):834-42. (Epub 2008 May 31).

Scranton et al. Mechanisms of anterior cruciate ligament neovascularization and ligamentization. Arthroscopy. 1998 October; 14(7):702-16.

Woo et al. Healing and repair of ligament injuries in the knee. J Am Acad Orthop Surg. 2000 November-December; 8(6): 364-72.

Woo et al. Tensile properties of the human femur-anterior cruciate ligament-tibia complex: The effects of specimen age and orientation. Am J Sports Med June 1991; 19(3): 217-225.

The invention claimed is:

1. A method of processing a bovine xenograft tendon for implantation into humans comprising the following steps utilizing cleaning agents:
   a. removing a xenoantigen from the tendon utilizing osmotic gradients, wherein said osmotic gradients comprise osmotic cycling from water, to saline and back to water,
   b. enhancing the strength of the tendon by non-enzymatic glycation, comprising treatment with a glucose sugar solution having a concentration ranging from between about 40 and 50 percent by weight (weight %),
   c. sterilizing the tendon, through exposure to an oxidizer and detergents,
   d. chemically rinsing the tendon,
   e. optionally decomposing residual cleaning agents from the tendon and
   f. optionally promoting the alkalinity of the tendon; wherein,
      one or more of said steps consists of contacting the tendon with said cleaning agents while tension is applied to the tendon and wherein said tension is between 60-75 pounds of force (between 267-334 Newtons) and further wherein the tendon is submerged within said cleaning agents in a treatment chamber during processing.

2. The method of claim 1, wherein the method steps are carried out in order from a-f.

3. The method of claim 1, wherein step a. has a Water to Chemical Ratio (WCR) greater than or equal to about 1.

4. The method of claim 1, wherein step b. has a Water to Chemical Ratio (WCR) less than about 1.

5. The method of claim 1, wherein step c. has a Water to Chemical Ratio (WCR) less than or equal to about 1.

6. The method of claim 1, wherein method steps a.-f. have a Water to Chemical Ratio (WCR) of about 0.90.

7. The method of claim 1, wherein the implant is taken from a santa gertrudis cow.

8. The method of claim 1, wherein the xenograft tendon comprises an anterior extensor tendon.

9. The method of claim 8, wherein the xenograft tendon comprises an Extensor Digitorum Medialis.

* * * * *